United States Patent
Schlom et al.

(10) Patent No.: US 8,609,395 B2
(45) Date of Patent: *Dec. 17, 2013

(54) AGONIST AND ANTAGONIST PEPTIDES OF CARCINOEMBRYONIC ANTIGEN (CEA)

(75) Inventors: Jeffrey Schlom, Potomac, MD (US); Elene Barzaga, Gaithersburg, MD (US); Sam Zaremba, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/399,471

(22) Filed: Feb. 17, 2012

(65) Prior Publication Data

US 2012/0149102 A1 Jun. 14, 2012

Related U.S. Application Data

(63) Continuation of application No. 12/752,768, filed on Apr. 1, 2010, now abandoned, which is a continuation of application No. 10/725,373, filed on Dec. 3, 2003, now Pat. No. 7,723,096, which is a continuation of application No. 09/529,121, filed as application No. PCT/US98/19794 on Sep. 22, 1998, now Pat. No. 6,756,038.

(60) Provisional application No. 60/061,589, filed on Oct. 10, 1997.

(51) Int. Cl.
  *C12N 15/63* (2006.01)
  *C12N 15/86* (2006.01)
  *C07H 21/04* (2006.01)
  *A61K 39/00* (2006.01)

(52) U.S. Cl.
  USPC ............ 435/252.3; 435/320.1; 536/23.1

(58) Field of Classification Search
  None
  See application file for complete search history.

(56) References Cited

U.S. PATENT DOCUMENTS

| | | | |
|---|---|---|---|
| 6,319,496 B1 | 11/2001 | Panicali et al. | |
| 6,969,609 B1 | 11/2005 | Schlom et al. | |
| 7,211,432 B2 | 5/2007 | Schlom et | |
| 7,723,096 B2 * | 5/2010 | Schlom et al. | 435/252.3 |
| 7,786,278 B2 * | 8/2010 | Parrington et al. | 536/23.1 |
| 2004/0019195 A1 | 1/2004 | Scholm et al. | |
| 2005/0101559 A1 | 5/2005 | Lawrence et al. | |

FOREIGN PATENT DOCUMENTS

| | | |
|---|---|---|
| EP | 0343946 | 11/1989 |
| WO | WO 91/02805 | 3/1991 |
| WO | WO 92/19266 | 11/1992 |
| WO | WO 00/34494 | 6/2000 |
| WO | WO 96/26271 | 8/2006 |

OTHER PUBLICATIONS

Anderton et al., *Immunology*, 104: 367-376 (2001).
Bakker et al., *Int. J. of Cancer*, 70: 302-309 (1997).
Bergmann et al., *J. Virol.*, 68(8): 5306-5310 (1994).
Bodey et al., *Anticancer Research*, 20: 2665-2676 (2000).
Chen et al., "CTL recognition of an altered peptide associated with asparagine bond rearrangement. Implications for immunity and vaccine design," *J. Immunol.*, 157 (3), 1000-1005 (1996).
Chen et al., "Response of a human T cell clone to a large panel of altered peptide ligands carrying single residue substitutions in an antigenic peptide: characterization and frequencies of TCR agonism and TCR antagonism with or without partial activation," *J. Immunol.*, 157 (9), 3783-3790 (1996).
Eisenlohr et al., *J. Exp. Med.*, 175: 481-487 (1992).
Engelhard, V.H, *Current Opinion Immunol.*, 6: 13-23 (1994).
England et al., "Molecular analysis of a heteroclitic T cell response to the immunodominant epitope of sperm whale myoglobin. Implications for peptide partial agonists," *J. Immunol.*, 155 (9), 4295-4306 (1995).
Gao et al., *J. Immunother*, 23: 643-653 (2000).
Gileadi et al., *Eur J. Immunol.* 29: 2213-2222 (1999).
Guo et al., *Nature*, 360: 364-366 (1992).
Hioe et al., *Molecular Immunology*, 32(10): 725-731 (1995).
Hudrisier et al., *J. of Biological Chemistry*, 271(30): 17829-17836 (1996).
Jameson et al., *Immunity*, 2: 1-11 (1995).
Madden et al., *Cell*, 75: 693-708 (1993).
Marchand et al., *Exp. Opin. Biol. Ther.*, 1(3): 497-510 (2001).
Marchand et al., *Int. J. of Cancer*, 80: 219-230 (1999).
Matsuoka et al., *J. of Immunology*, 157(11): 4837-4843 (1996).
NCBI Blast search Accession P06731, 1987.
Nijman et al., *Eur. J. of Immunolgy*, 23: 1215-1219 (1993).
Parkhurst et al., *J. of Immunology*, 157: 2539-2548 (1996).
Perkins et al., *J. Immunol.*, 146: 2137-2144 (1991).
Pogue et al., *Proc. Natl. Acad. Sci. USA*, 92: 8166-8170 (1995).
Ramensee et al., *Immunogenetics*, 41: 178-228 (1995).
Ras et al., *Hum. Imm.*, 53: 81-89 (1997).
Ruppert et al., *Bering Inst. Mitt*, 94: 48-60 (1994).
Shastri et al., *J. Immunol.* 155: 4339-4346 (1995).
Sigal et al., *Molecular Immunology*, 32 (9): 623-632 (1995).
Sigal et al., *Molecular Immunology*, 33 (17/18): 1323-1333 (1996).
Skipper et al., "An HLA-A2-restricted tyrosinase antigen on melanoma cells results from posttranslational modification and suggests a novel pathway for processing of membrane proteins," *J. Exp. Med.*, 183 (2), 527-534 (1996).
Theobald et al., *J. Exp. Med.*, 6: 1017-1028 (1998).
Toutirais et al., *J. Immunother.*, 33(4): 402-413 (2010).
Tsang et al., *Clinical Cancer Res.*, 12: 2349 (1997).
Tsang, et al., *J. Natl. Cancer Inst.*, 87: 982-990 (1995).
Wang et al., *Cell Immunol.*, 143: 284-297 (1992).
Zaremba et al., *Cancer Research*, 57: 4570-4577 (1997).

* cited by examiner

*Primary Examiner* — Gerald R Ewoldt
*Assistant Examiner* — Marianne DiBrino
(74) *Attorney, Agent, or Firm* — Leydig, Voit & Mayer, Ltd.

(57) ABSTRACT

The invention provides a polypeptide comprising an agonist of a MHC Class I binding native sequence having amino acid substitution(s) and enhanced immunogenicity compared to the native sequence. The invention provides DNA encoding the polypeptide, as well as vectors and cells comprising the DNA and methods comprising the administration of the polypeptide.

15 Claims, 10 Drawing Sheets

SEQUENCE LISTING

```
<160> NUMBER OF SEQ ID NOS: 12

<210> SEQ ID NO 1
<211> LENGTH: 9
<212> TYPE: PRT
<213> ORGANISM: Homo sapiens

<400> SEQUENCE: 1

Tyr Leu Ser Gly Ala Asn Leu Asn Leu
1               5

<210> SEQ ID NO 2
<211> LENGTH: 9
<212> TYPE: PRT
<213> ORGANISM: Homo sapiens

<400> SEQUENCE: 2

Tyr Leu Ser Gly Ala Asp Leu Asn Leu
1               5

<210> SEQ ID NO 3
<211> LENGTH: 9
<212> TYPE: PRT
<213> ORGANISM: Homo sapiens

<400> SEQUENCE: 3

Tyr Leu Ser Gly Ala Asp Ile Asn Leu
1               5

<210> SEQ ID NO 4
<211> LENGTH: 9
<212> TYPE: PRT
<213> ORGANISM: Homo sapiens

<400> SEQUENCE: 4

Tyr Leu Ser Gly Ala Asn Ile Asn Leu
1               5

<210> SEQ ID NO 5
<211> LENGTH: 9
<212> TYPE: PRT
<213> ORGANISM: Homo sapiens

<400> SEQUENCE: 5

Tyr Leu Ser Gly Ala Cys Leu Asn Leu
1               5

<210> SEQ ID NO 6
<211> LENGTH: 27
<212> TYPE: DNA
```

```
<213> ORGANISM: Homo sapiens

<400> SEQUENCE: 6
tacctttcgg gagcgaacct caacctc                                              27

<210> SEQ ID NO 7
<211> LENGTH: 27
<212> TYPE: DNA
<213> ORGANISM: Homo sapiens

<400> SEQUENCE: 7
tacctttcgg gagcggacct caacctc                                              27

<210> SEQ ID NO 8
<211> LENGTH: 27
<212> TYPE: DNA
<213> ORGANISM: Homo sapiens

<400> SEQUENCE: 8
tacctttcgg gagcggacat caacctc                                              27

<210> SEQ ID NO 9
<211> LENGTH: 9
<212> TYPE: PRT
<213> ORGANISM: Homo sapiens

<400> SEQUENCE: 9

Tyr Leu Asn Val Gln Asp Leu Asn Leu
1               5

<210> SEQ ID NO 10
<211> LENGTH: 9
<212> TYPE: PRT
<213> ORGANISM: Homo sapiens

<400> SEQUENCE: 10

Tyr Leu His Asp Pro Glu Phe Asn Leu
1               5

<210> SEQ ID NO 11
<211> LENGTH: 27
<212> TYPE: DNA
<213> ORGANISM: Homo sapiens

<400> SEQUENCE: 11
tacctttcgg gagcgaacat caacctc                                              27

<210> SEQ ID NO 12
<211> LENGTH: 27
<212> TYPE: DNA
<213> ORGANISM: Homo sapiens

<400> SEQUENCE: 12
tacctttcgg gagcgtgtct caacctc                                              27
```

AGONIST AND ANTAGONIST PEPTIDES OF CARCINOEMBRYONIC ANTIGEN (CEA)

CROSS-REFERENCE TO RELATED APPLICATIONS

Figure 1A:
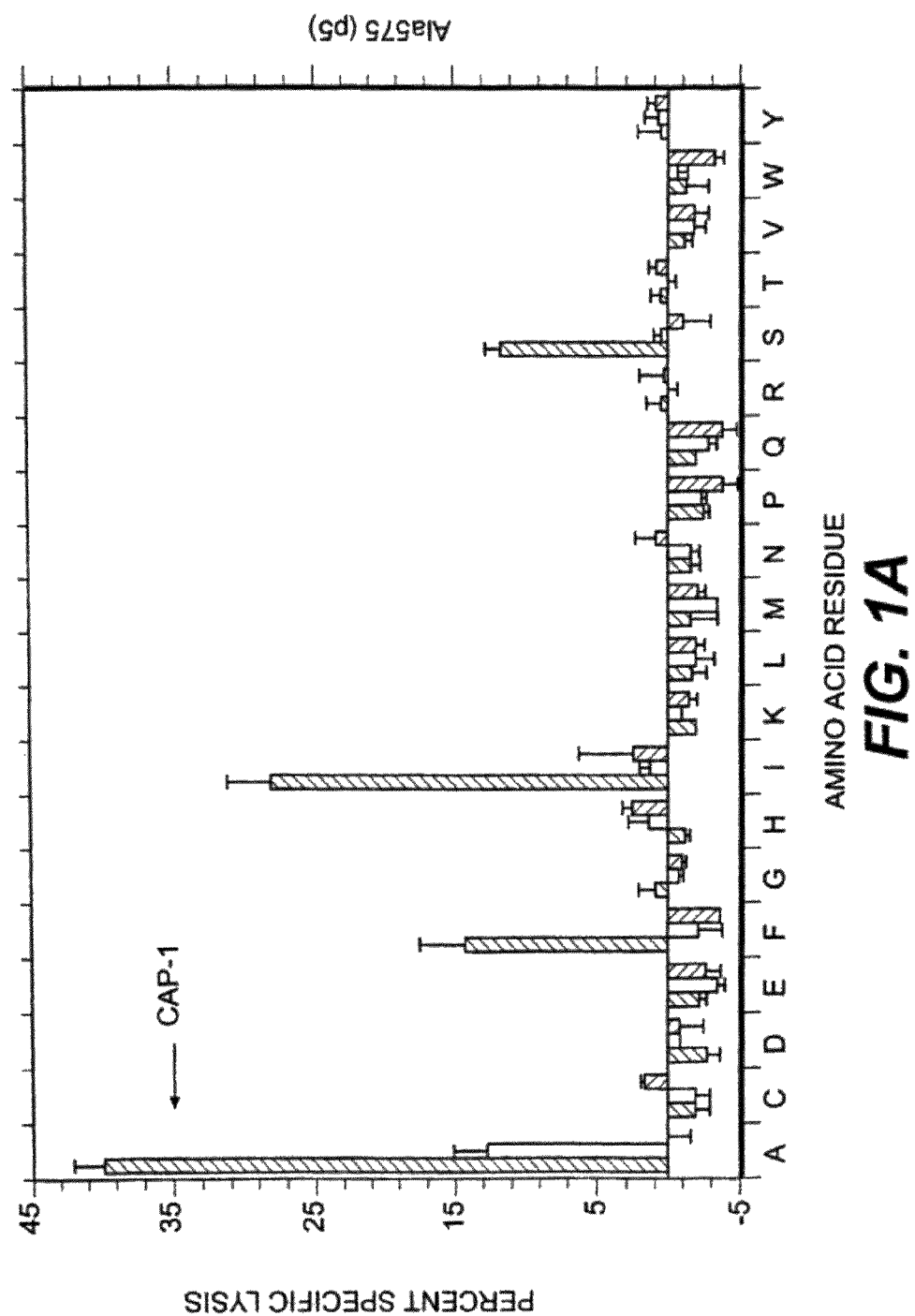
Figure 1B:
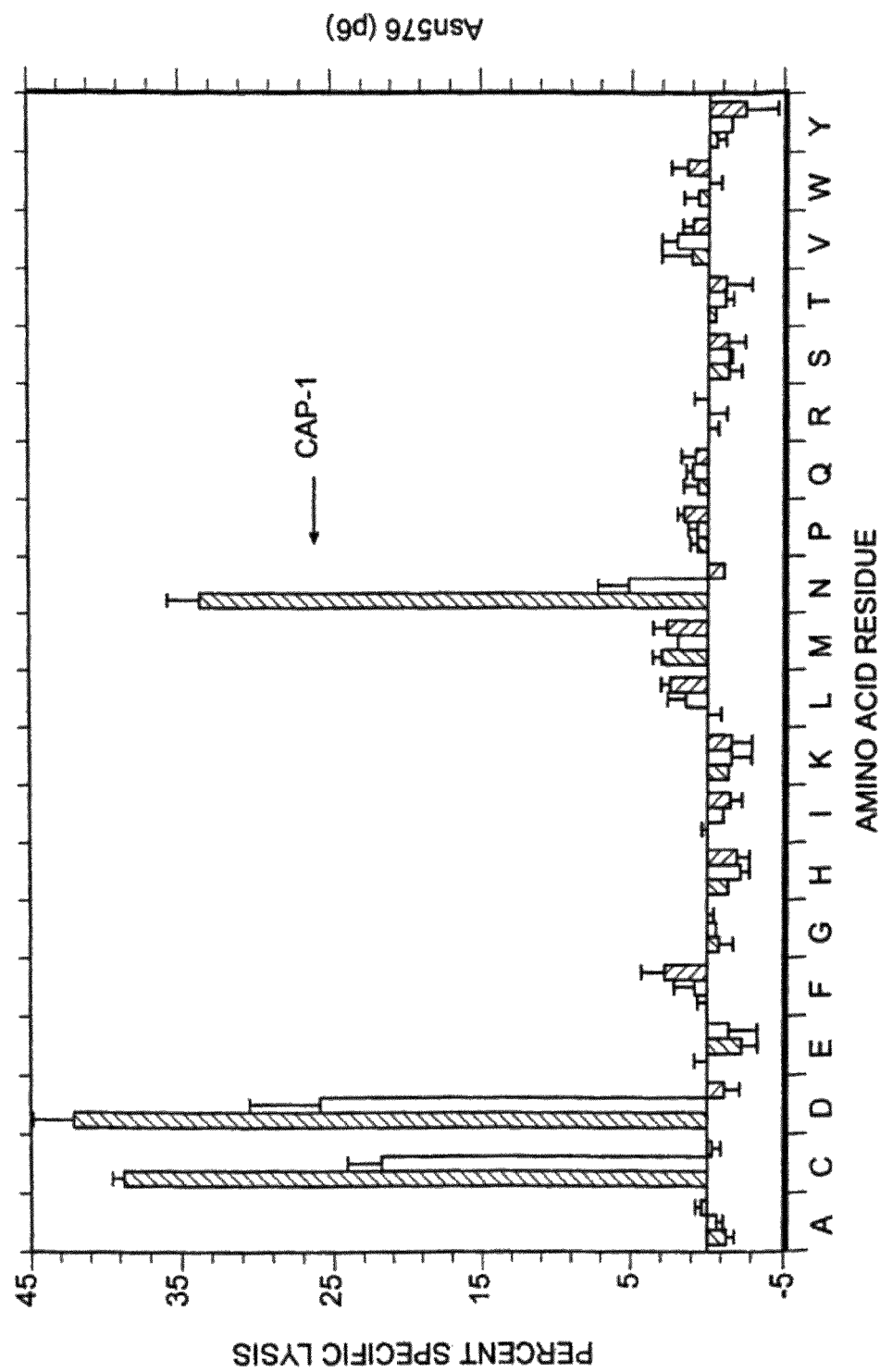
Figure 1C:
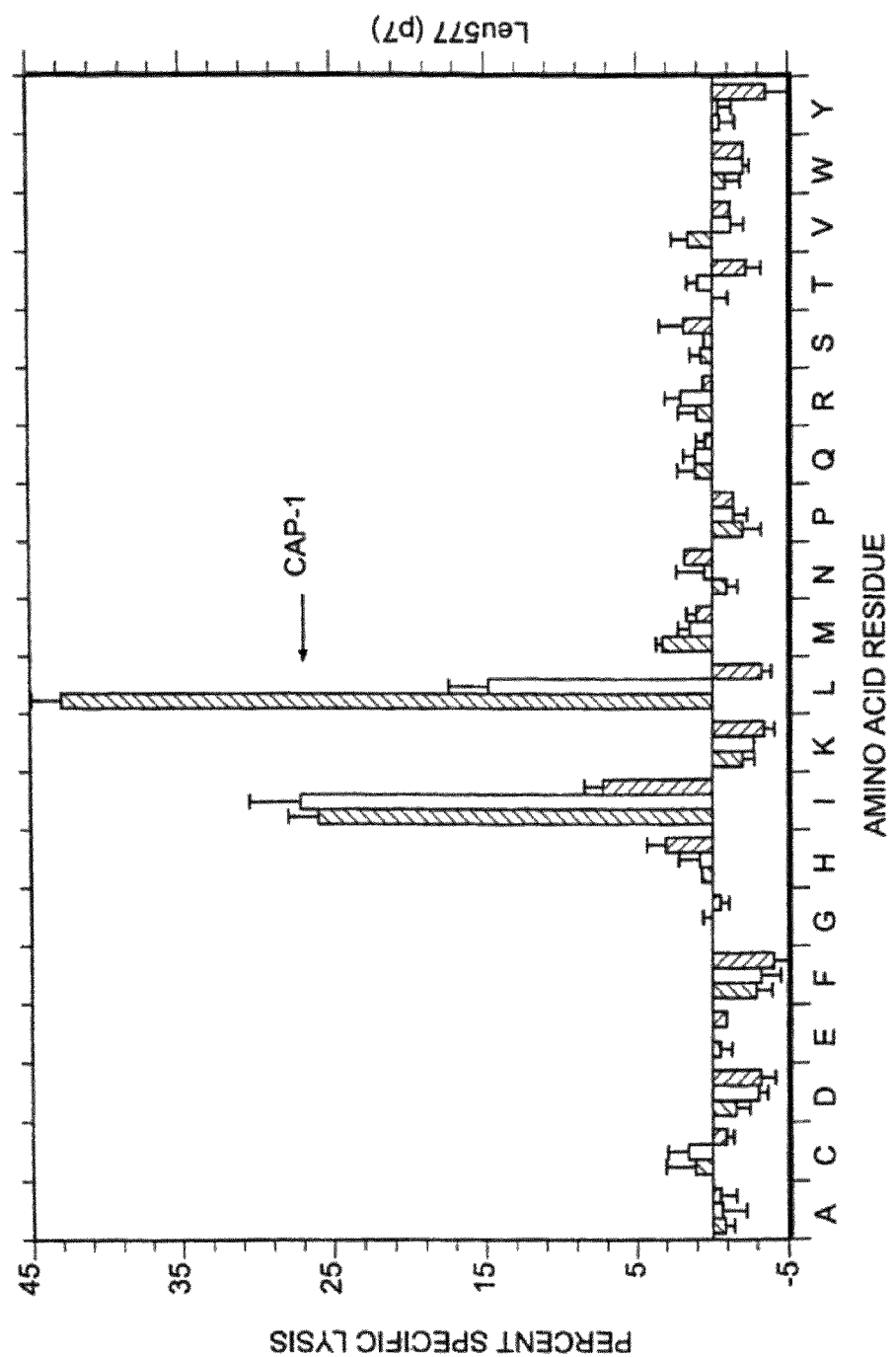
Figure 1D:
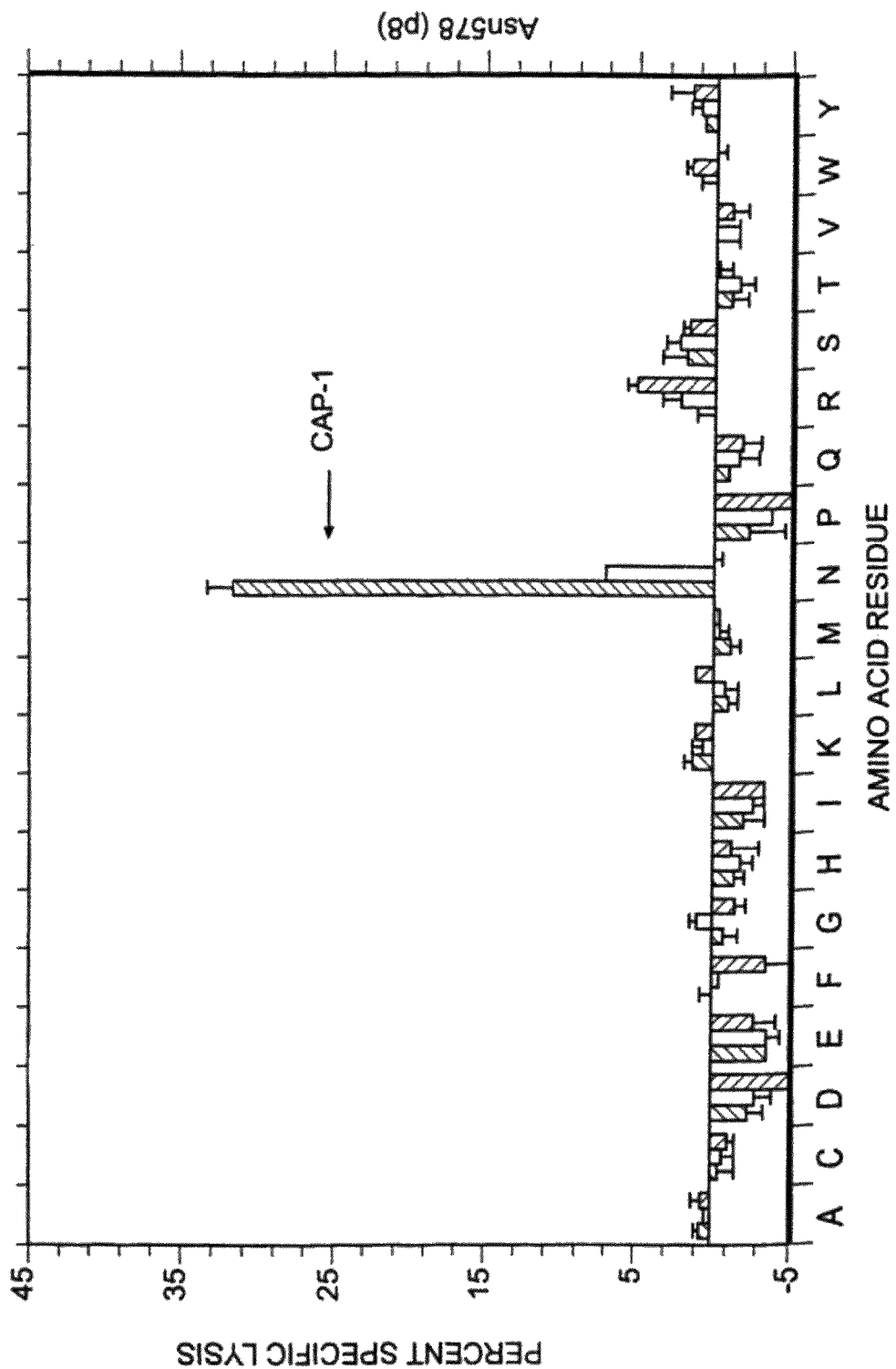

This patent application is a continuation of U.S. patent application Ser. No. 12/752,768, filed Apr. 1, 2010, which is a continuation of U.S. patent application Ser. No. 10/725,373, filed Dec. 3, 2003, now U.S. Pat. No. 7,723,096, which is a continuation of U.S. patent application Ser. No. 09/529,121, filed Jun. 13, 2000, now U.S. Pat. No. 6,756,038, which is the U.S. national phase application of PCT/US98/19794, filed Sep. 2, 1998, which claims the benefit of U.S. Provisional Patent Application No. 60/061,589, filed Oct. 10, 1997, which applications are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,238 Byte ASCII (Text) file named "707350_ST25.txt," created on Dec. 27, 2010.

FIELD OF THE INVENTION

The present invention relates to the preparation and use of peptides that can act as agonists and antagonists of human carcinoembryonic antigen (CEA). More specifically, the agonist peptide according to the present invention can be used as an immunogen, either alone, or in prime and boost protocols with other immunogens such as rV-CEA, for a variety of neoplastic conditions. These may include colorectal cancer, lung cancer, pancreatic cancer, and breast cancer. Thus, the present invention also relates to the production and use of vaccines against cancer. Peptide agonists according to the present invention can also be used to facilitate propagation of T cells, for example, from vaccinated patients, for adoptive transfer studies. Peptide antagonists according to the present invention find utility in suppressing autoimmune responses, such as those involving T cells, when such responses occur in vaccinated patients. Thus, the present invention also relates to the production and use of vaccines against autoimmune diseases, especially those mediated by lymphocytes and other antigen presenting cells.

BACKGROUND OF THE INVENTION

A major challenge of modern cancer immunotherapy is the identification of cytotoxic T lymphocyte (CTL) epitopes from defined tumor-associated antigens (TAA) that promote lysis of tumor cells. The majority of antigens on human cancers are not tumor specific and are overexpressed in malignant cells as opposed to cells of normal tissues. Therefore, immunity to cancer in humans may rest mostly on the development of an effective immune response mainly directed to self-molecules qualitatively common to all cell types.

Human carcinoembryonic antigen (CEA) is a 180 kD glycoprotein expressed on the majority of colon, rectal, stomach and pancreatic tumors (1), some 50% of breast carcinomas (2) and 70% of lung carcinomas (3). CEA is also expressed in fetal gut tissue, and to a lesser extent on normal colon epithelium. The immunogenicity of CEA has been ambiguous, with several studies reporting the presence of anti-CEA antibodies in patients (4-7) while other studies have not (8-10). CEA was first described as a cancer specific fetal antigen in adenocarcinoma of the human digestive tract in 1965 (Gold, P. and Freeman, S. O. (1965) Exp. Med. 121:439-462). Since that time, CEA has been characterized as a cell surface antigen produced in excess in nearly all solid tumors of the human gastrointestinal tract. The gene for the human CEA protein has been cloned. (Oikawa et al (1987) Biochim. Biophys. Res. 142:511-518; European Application No. EP 0346710).

Recently, the first evidence was reported of a human CTL response to CEA (11). This CAP1 peptide showed the highest level of T2 cell binding among the various CEA peptides tested with stimulation of the T cells resulting in the generation of cytotoxic T cell lines. We have identified a 9-mer peptide, designated CAP1 (with the sequence YLSGANLNL) (SEQ. ID NO: 1), on the basis of binding to HLA-A2, and the ability to generate specific CTL from peripheral blood mononuclear cells (PBMC) from carcinoma patients immunized with a recombinant vaccinia virus expressing CEA (rV-CEA). For example, peripheral blood lymphocytes (PBLs) from 5 patients showed signs of T cell response to CAP1 peptide after immunization with rV-CEA. Two other laboratories have since generated CAP1 specific CTL in vitro employing peptide pulsed dendritic cells as antigen presenting cells (APC) (12). It has also recently been reported (13) that CAP1 specific CTL can be generated from PBMC from carcinoma patients immunized with the avipox recombinant ALVAC-CEA. Several groups have also reported the generation of anti-CEA antibodies and CEA specific proliferative T cell responses following immunization with either an anti-Id to an anti-CEA monoclonal antibody (MAb) (14), recombinant CEA protein (15), or rV-CEA (16).

Several investigators have introduced CTL to tumor associated and viral antigens by in vitro stimulation of PBMC with an immunodominant peptide. Recent work with the gp100 melanoma antigen (17-19), an HIV polymerase peptide (20) and the papilloma virus tumor antigen E6 (21) demonstrated enhanced immunogenicity after modifications to the peptide sequences. In these studies, replacements were at anchor positions and were intended to increase binding to murine or human MHC antigens. This approach was based on a demonstrated correlation between immunogenicity and peptide binding affinity to class I MHC (major histocompatibility complex) molecules for viral antigen epitopes (22).

Previous investigators have also worked with fragments of CEA. Thus, Shively (1989), in a European patent publication (EP No. 0343946 A2) reports a number of CEA fragments that include a unique epitope (as defined by its reactivity with an antibody). The latter CEA fragment is 177 amino acid residues long and contains the 9-mer sequence of CAP1. However, no shorter CEA fragments that include the CAP1 sequence were described.

In sum, the use of rV-CEA alone as an agent for boosting the CEA-specific immune response of rV-CEA suffers from the drawback of stimulating an immune response to vaccinia virus. However, the novel combination of rV-CEA and CAP1 suggested itself to us as a "second generation protocol" for the treatment of cancer patients.

It is an accepted principle that when an immunogenic peptide is modified in a conserved manner (e.g., a hydrophobic amino acid is substituted with a hydrophobic amino acid) the modified peptide is likely to have similar immunogenic activity based upon the maintenance of the molecule's shape, charge and hydrophobic character.

More specifically, a study by Madden (33) has identified specific amino acid preferences in peptides for MHC-complexing, a precursor step to T cell recognition. Madden as well as other investigators (31) suggest that specific amino acid positions in peptides are available for T cell recognition.

Skipper et al. (40) describes the identification and characterization of a naturally-occurring peptide epitope of tyrosinase, wherein the peptide sequence differs from that which is predicted from the DNA. This modified peptide is recognized by tyrosinase-specific human cytotoxic T-lymphocytes ("CTL") more effectively than the direct translation product and is the only one of the two peptides to be presented by HLA-A2.1 molecules on the cell surface. The modification is a substitution of an asparagine with an aspartic acid. The authors propose that the asparagine is N-glycosylated in the endoplasmic reticulum during protein synthesis and is deamidated post-translationally.

In the case of CAP1, the primary and secondary anchors at positions 2, 9, and 1 are already occupied by preferred amino acids and so a different approach was taken to improve peptide immunogenicity by attempting to enhance its ability to bind to the TCR. It appeared to us that by altering amino acid residues expected to contact the TCR one could generate an analog of CAP1 with substitutions at non-MHC anchor positions. Such an analog might then represent a T cell enhancer agonist capable of stimulating CTL more efficiently than the native peptide. Previous results supported the concept that some peptide analogs could act as T cell antagonists by inhibiting responses to the antigenic peptide (23-29). Such inhibition was shown to be TCR specific and could not be explained by competition for peptide binding to the MHC protein. Analogously, a peptide enhancer agonist would be an analog that increased the effector function without accompanying increases in MHC binding. We therefore sought to increase CAP1 immunogenicity by analyzing panels of analogs containing single amino acid substitutions to residues we predicted would interact with the T cell receptor (TCR) of CAP1-specific CTL. The present invention relates to the construction of a novel T cell enhancer agonist for the CAP1 peptide, the first such example for a human CTL epitope.

SUMMARY OF THE INVENTION

The present invention relates to the identification of peptides which are single or double amino acid changes from the CAP-1 peptide sequence. The CAP-1 peptide has been identified as a highly immunogenic epitope of the carcinoembryonic antigen (referred to herein as "CEA"), which is capable of stimulating CEA-specific cytolytic T-cell ("CTL") responses. CEA is a cell surface antigen found in abundance on several types of cancer cells. Thus, peptides of CEA capable of stimulating a cytolytic CTL response, such as CAP-1 are potential immunogens for use in cancer immunotherapy.

Some of the peptides of the present invention are agonists of CAP-1 and CEA; that is, they facilitate the interaction between the MHC-complex of the antigen-presenting cell and the T-cell receptor ("TCR") complex of the T-cell. Thus, these peptides can serve as immunogens to treat and/or vaccinate patients with CEA-expressing cancers. Also, these peptides may be used to stimulate T-cells in culture for adoptive transfer of T-cells to cancer patients. Four such peptides have amino acid sequences:

```
                                     (SEQ. ID NO: 2)
(1)    YLSGADLNL       (Agonist CAP1-6D);

(SEQ. ID NO: 3)
(2)    YLSGADINL       (Agonist CAP1-6D, 7I);
```

-continued

```
                                     (SEQ. ID NO: 4)
(3)    YLSGANINL       (Agonist CAP1-7I);
and (SEQ. ID NO.: 5)
(4)    YLSGACLNL       (agonist CAP1-6C).
```

The underlined amino acids identify the amino acids changes from the CAP-1 peptide sequence. Peptides CAP1-6D and CAP1-6D, 7I are especially preferred peptides according to the present invention and have enhanced activity as compared to CAP-1 activity. Peptides CAP1-7I and CAP1-6C have activity similar to CAP-1.

Other peptides according to the present invention function as antagonists of CEA; that is, they reduce or eliminate CEA-specific T-cell activation and killing which occur through interactions of the MHC-peptide complex and TCR complex.

The present invention encompasses kits comprising an agonist peptide and a vector comprising a gene encoding CEA or a recombinantly produced CEA protein. Moreover, the kit may include an immunostimulatory molecule.

The present invention also encompasses kits comprising an antagonist peptide alone or in combination with an immunosuppressive agent.

Another object of the present invention is a pharmaceutical composition comprising one or more agonist peptides alone or in combination with an immunostimulatory molecule and a pharmaceutically acceptable carrier.

Another object of the present invention is a pharmaceutical composition comprising one or more antagonist peptides alone or in combination with an immunosuppressing agent and a pharmaceutically acceptable carrier.

The present aspect of the present invention is a nucleic acid sequence encoding at least one agonist peptide or encoding at least one antagonist peptide.

Another aspect of the invention is a vector comprising a nucleic acid sequence encoding at least one agonist peptide or a nucleic acid sequence encoding at least one antagonist peptide and host cells comprising such vectors.

Another aspect of the present invention relates to the use of these peptides in cancer immunotherapy. The agonist peptides are useful in stimulating a cytolytic immune response to CEA, resulting tumor reduction and/or prevention. Accordingly, the present invention also relates, to a method of treating cancer patients with the peptides as well as a cancer vaccine. The antagonist peptides are useful in methods of controlling autoimmune response to CEA or CAP-1.

Yet another aspect of the present invention is an agonist-pulsed antigen presenting cell.

BRIEF DESCRIPTION OF THE DRAWINGS

FIG. 1A-1D: Effect of single amino acid substitutions in CEA CAP1 peptide on lysis by CEA CTL T-Vac8 C1R-A2 cells were labeled with $^{111}$In and incubated for 1 hour in round bottom wells (2,000/well) with each substituted peptide at 1 (solid), 0.1 (open) and 0.01 (hatched) μg/ml. T-Vac8 CTL were added at E:T=1.45:1 and isotope release was measured after 4 hours. Spontaneous release was determined for each peptide at 1 μg/ml. All assays were performed in triplicate. FIGS. 1A-1D depict substitutions at positions p5 through p8, respectively. Amino acids are designated by the single letter code; the amino acid encoding the native CAP1 sequence is indicated in each figure and along the right-hand margin.

FIGS. 2A and 2B: CAP1 and analogs show different sensitivity to CEA CTL T-Vac8 cytotoxicity FIG. 2A T2 and FIG. 2B C1R-A2 target cells were labeled with $^{51}$Cr and incubated in round-bottomed 96 well plates (10,000/well) with CAP1 (○) or substituted peptides CAP1-6D (□) or CAP1-7I (◇) at the indicated concentrations. After 1 hour, T-Vac8 CTL were added at E:T=2.5:1 and isotope release was determined after 4 hours. All assays were done in triplicate. NCA571 (◇) is a 9-mer peptide obtained after optimal alignment of CEA with the related gene NCA (11).

Figure 3A:
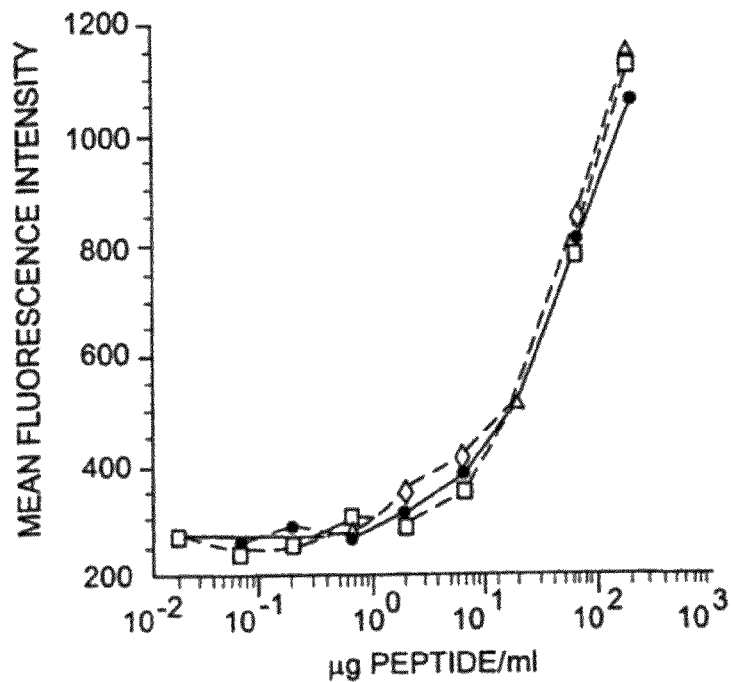
Figure 3B:
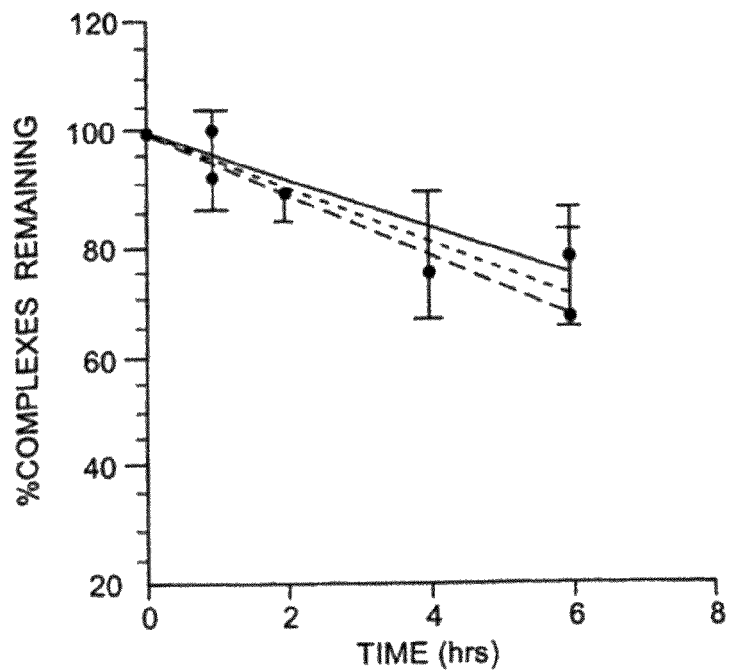

FIG. 3: Effect of single amino acid substitutions in CAP1 peptide on binding to and stability of HLA-A2 complexes T2 cells were collected in serum free medium then incubated overnight (10$^6$ well) with peptides CAP1(⊙), CAP1-6D (□), or CAP1-7I (◇) at the indicated concentrations. Cells were collected and assayed for cell surface expression of functional HLA-A2 molecules by staining with conformation sensitive MAb BB7.2, HLA specific antibody W6/32 (not shown) and isotype control Ab MOPC-195 (not shown). Mean fluorescent intensity was determined on a live, gated cell population. Figure insert: Cells were incubated with peptide at 100 μg/ml overnight, then washed free of unbound peptide and incubated at 37° C. At the indicated times, cells were stained for the presence of cell surface peptide-HLA-A2 complexes. The error bars indicate SEM for two experiments.

Figure 4A:
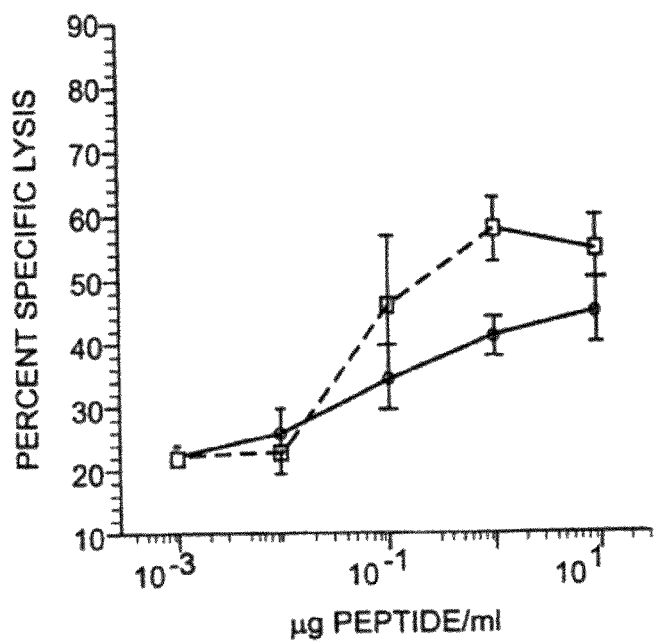
Figure 4B:
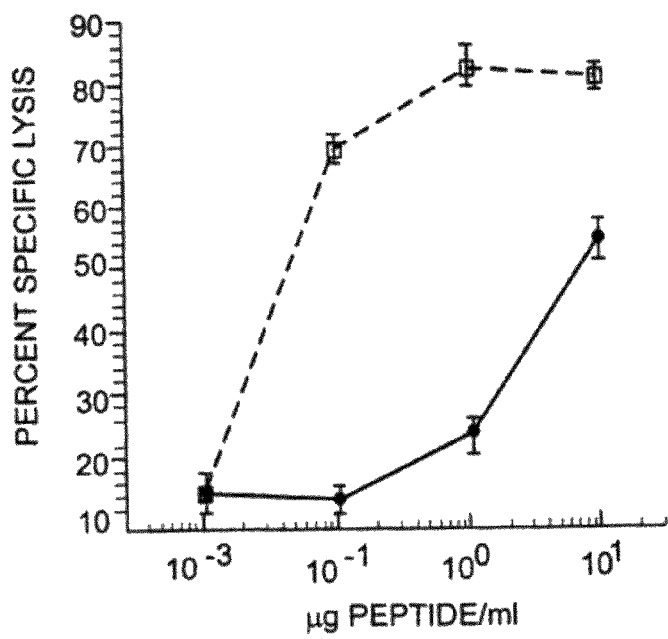

FIGS. 4A and 4B: CTL generated from apparently healthy individuals with CAP1-6D peptide recognize CAP1 and CAP1-6D CTL lines (designated T-N1 and T-N2) were generated with CAP1-6D and were assayed for peptide specificity. T-N 1 was assayed after 5 cycles of stimulation at an effector to target ratio of 20:1 (FIG. 4A). T-N2 was assayed after 10 cycles at an effector to target ratio of 15:1 (FIG. 4B). $^{51}$Cr-labeled C1R-A2 targets (5,000/well) were incubated with the indicated amount of CAP1 (○) or CAP1-6D (□) peptide. After 4 hours the amount of isotope release was determined in a gamma counter. Values were determined from triplicate cultures.

Figure 5A:
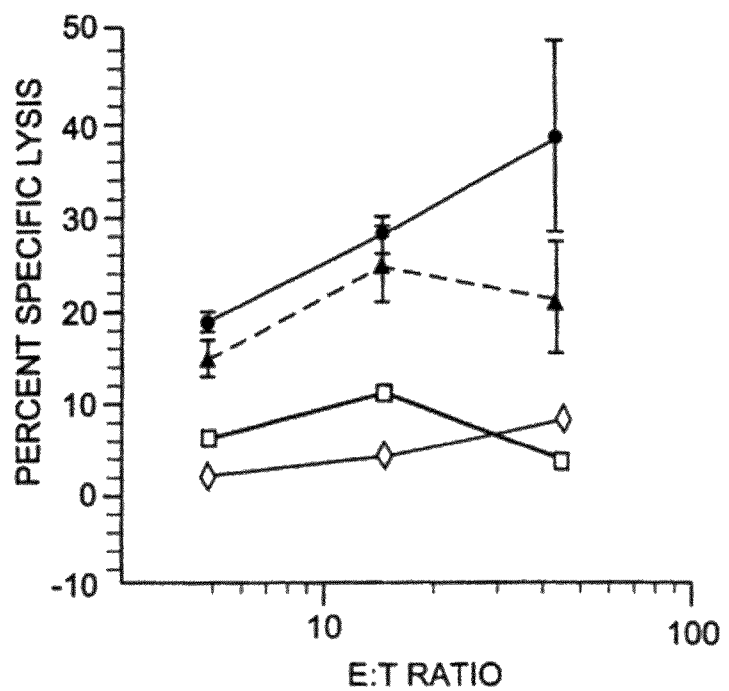
Figure 5B:
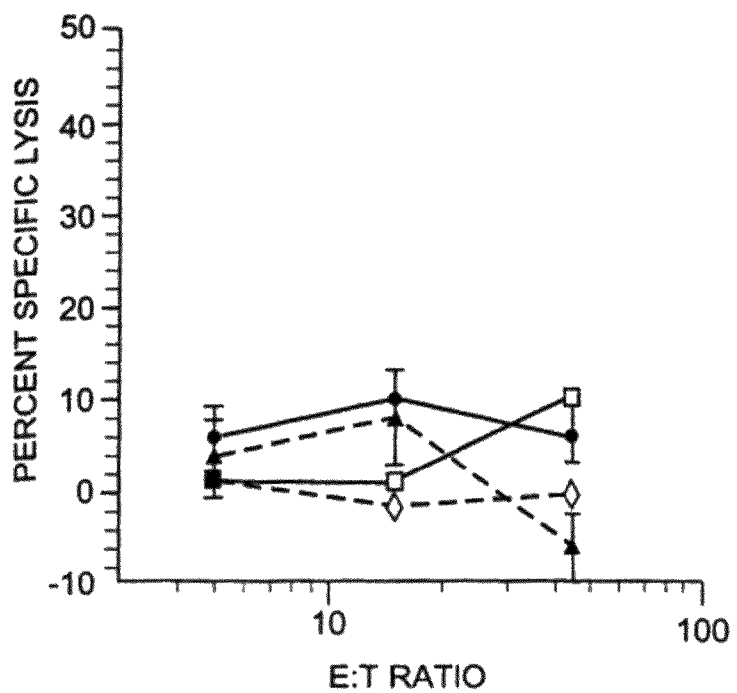

FIGS. 5A and 5B: CAP1-6D, but not CAP1 generated T cell lines from apparently healthy donors recognize tumor cells expressing endogenous CEA CAP1-6D generated T-N2 CTL (FIG. 5A) and T cells generated with native CAP1 (FIG. 5B), were assayed after 9 cycles of in vitro stimulation against tumor targets SW480 and SW1463 (CEA$^+$, HLA-A2$^+$, ⊙ and ⋏ respectively), SKmel24 (CEA$^-$, -A2$^+$, □) and K562 (◇). Tumor cells were cultured for 72 hours in the presence of γ-IFN to up regulate HLA. Cells were trypsinized and labeled with $^{51}$Cr and incubated (5,000 cells/well) with T-N2 CTL at increasing effector to target ratios. Cultures were incubated for 4 hours and the amount of isotope release determined in a gamma counter. Values were determined from triplicate cultures.

Figure 6:
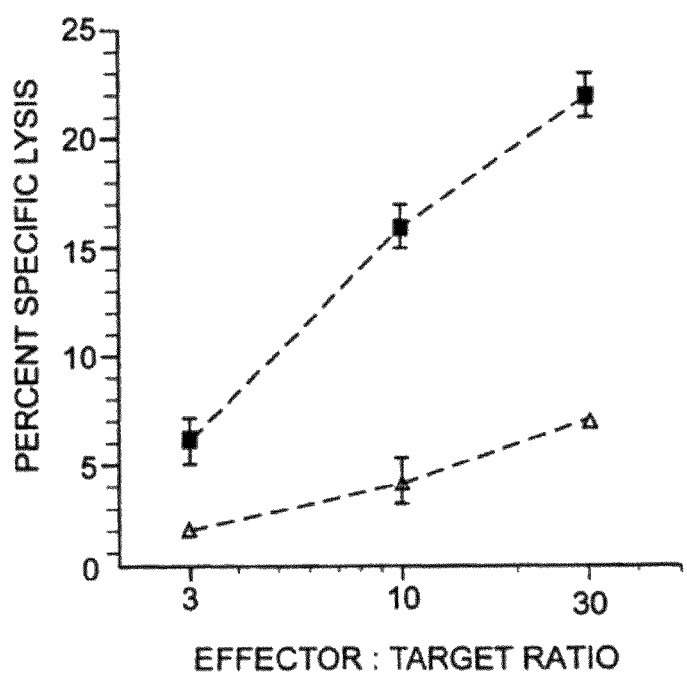

FIG. 6: MHC-class 1 A2.1 restriction of CTL line (T-N2) derived from CAP1-6D agonist CTL line T-N2 was used as an effector for the human colon carcinoma SW837 target cell. SW837 is CEA positive and HLA-A2.1 negative. SW837 were infected at an MOI of 10:1 with either a recombinant vaccinia containing the A2.1 transgene (⊞) or wild type vaccinia (Δ).

Figure 7A:
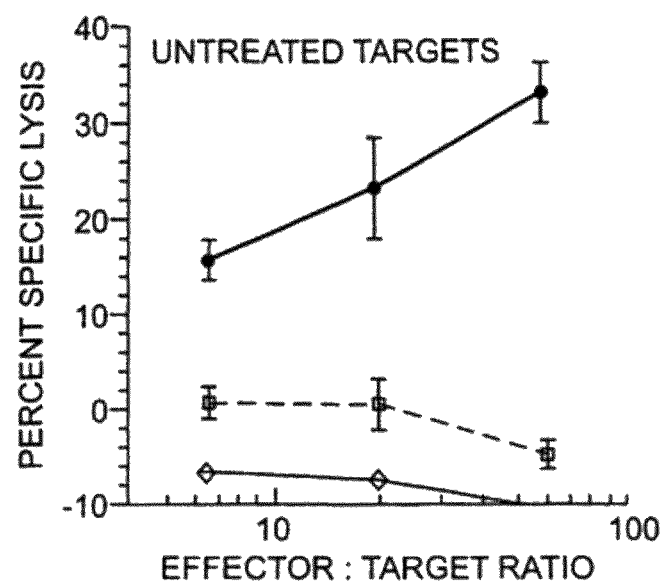
Figure 7B:
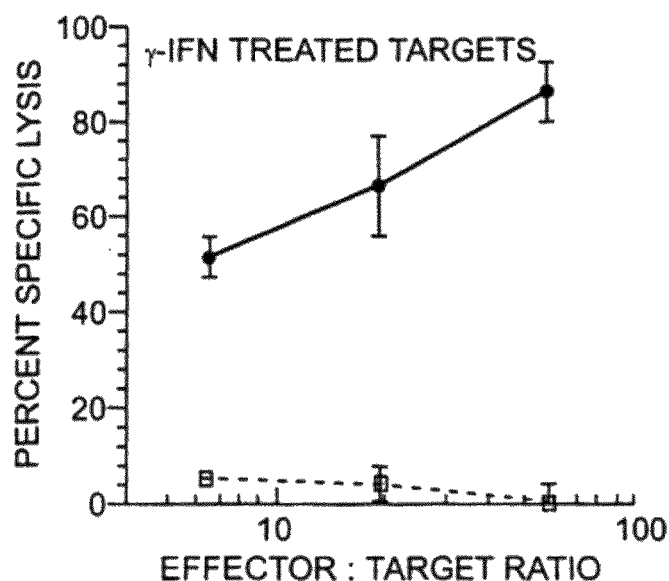

FIGS. 7A and 7B: CTL generated with CAP1-6D lyse CEA positive, HLA-A2 positive tumors: Effect of IFN upregulation The T-N1 CTL generated with CAP1-6D were assayed against various tumor cell lines: SW480 (CEA$^+$ and HLA-A2$^+$, ○), SW1116 (CEA$^+$ but -A2$^-$, □) and CaOV3 (CEA$^-$ but -A2$^+$, ◇). Tumor cells were cultured 72 hours in the absence (FIG. 7A) or presence (FIG. 7B) of γ-IFN, trypsinized and labeled with $^{51}$Cr then incubated (5,000 cells/well) with T-N1 CTL at increasing effector to target ratios. Cultures were incubated for 4 hours and the amount of isotope release determined in a gamma counter. Values were determined from triplicate cultures.

DETAILED DESCRIPTION OF THE INVENTION

The invention is an peptide agonist of the native CEA epitope, CAP-1 (SEQ. ID. NO: 1), as well as antagonists of SEQ. ID NO: 1. The agonist is characterized by its ability to elicit antigen specific cytotoxic T lymphocytes which inhibit the growth or kill carcinoma cells expressing CEA or CEA epitopes. An antagonist of the present invention serve to inhibit or prevent CEA specific immune responses. Such peptides may be used to shut off any unwanted immune responses to CAP-1 or CEA. One example for such use of an antagonist is to control any possible autoimmune response that may occur during cancer immunotherapy, where the therapy has killed off tumor cells and begins to attack normal cells expressing CEA. In accordance with the present invention an antagonist would advantageously prevent extensive damage to normal tissue.

The peptide agonists of the present invention comprise about 8-13 amino acids, preferably 9-10 amino acids. In a preferred embodiment, the agonist peptide of the present invention comprises at least one amino acid substitution at a non-anchor position. In one embodiment, the agonist comprises a sequence with a substitution at position 6 compared to the native CAP-1 (SEQ. ID NO: 1). In another embodiment the agonist comprises a sequence with an amino acid substitution at position 7 compared to the native CAP-1 (SEQ. ID NO: 1). In yet another embodiment, the agonist comprises a sequence with an amino acid substitution at position 6 and at position 7 compared to the native CAP-1. The substituted amino acid serves to enhance the interaction of the TCR complex on the cytotoxic T lymphocytes with the peptide-MHC antigen ligand complex. Such enhanced interaction results in greater effector function by the cytotoxic T lymphocytes.

An example of a substitution includes Asp and Cys at position 6 or an Ile at position 7.

In one embodiment, the peptide agonist comprises the following, amino acid sequence:

| | Amino Acid | |
|---|---|---|
| Position | 1 2 3 4 5 6 7 8 9 | |
| Native CAP-1 Peptide | Y L S G A N L N L | (SEQ. ID NO: 1) |
| Agonist | Y L S G A <u>D</u> L N L | (SEQ. ID NO: 2) |
| Agonist | Y L S G A <u>D</u> <u>I</u> N L | (SEQ. ID NO: 3) |
| Agonist | Y L S G A N <u>I</u> N L | (SEQ. ID NO: 4) |
| Agonist | Y L S G A <u>C</u> L N L | (SEQ. ID NO: 5) |

The agonist peptide of the present invention may be obtained by recombinant DNA technology or by chemical peptide synthesis.

The agonist peptide may be formulated into a pharmaceutical composition in combination with a pharmaceutically acceptable carrier for use as an immunogen in a mammal, preferably a human. The composition may further comprise one or more other constituents to enhance the immune response which include but are not limited to immunostimulatory molecules such as interleukin 2, interleukin 6, interleukin 12, interferon gamma, tumor necrosis factor alpha, GM-CSF, B7.1, B7.2, ICAM-1, LFA-3, CD72, and cyclophosphamide.

The agonist peptide is administered to a mammal in an amount effective in generating a CEA specific immune response, preferably a cellular immune response. The efficacy of the mutant ras peptide as an immunogen may be determined by in vivo or in vitro parameters as are known in the art. These parameters include but are not limited to antigen specific cytotoxicity assays, regression of tumors expressing CEA or CEA epitopes, inhibition of cancer cells expressing CEA or CEA epitopes, production of cytokines and the like.

At least one or more agonist peptides may be administered in a dose of about 0.05 mg to about 10 mg per vaccination of the mammal, preferably about 0.1 mg to about 5 mg per vaccination. Several doses may be provided over a period of weeks as indicated. In one embodiment a dose is provided every month for 3 months. The agonist peptide may be administered alone or in combination with adjuvants, incorporated into liposomes (U.S. Pat. Nos. 5,643,599; 5,464,630; 5,059,421; 4,885,172), with cytokines, biological response modifiers, or other reagents in the art that are known to enhance immune response. Adjuvants include but are not limited to RIBI Detox™, QS21, alum and incomplete Freund's adjuvant. In one embodiment, the mutant ras peptide is administered in combination with Detox™ (RIBI Immunochem Research, Hamilton, Mont.). RIBI Detox™ contains as active ingredients the cell wall skeleton from *Mycobacterium phlei* and monophosphoryl lipid A from *Salmonella minnesota* R595 prepared as an oil-in-water emulsion with squalene and tween 80.

The agonist peptides may also be conjugated to helper peptides or to large carrier molecules to enhance the immunogenicity of the peptide. These molecules include but are not limited to influenza peptide, tetanus toxoid, tetanus toxoid CD4 epitope, *Pseudomonas* exotoxin A, poly-L-lysine, a lipid tail, endoplasmic reticulum (ER) signal sequence and the like.

The peptides of the present invention may also be conjugated to an immunoglobulin molecule using art accepted methods. The immunoglobulin molecule may be specific for a surface receptor present on tumor cells but absent or in very low amounts on normal cells. The immunoglobulin may also be specific for a specific tissue. Such a peptide-immunoglobulin conjugate allows for targeting of the peptide to a specific tissue and/or cell.

Another effective form of the agonist peptide for generating an peptide specific immune response in a mammal is an agonist peptide-pulsed antigen presenting cell. The antigen presenting cells include but is not limited to dendritic cells, B lymphocytes, monocytes, macrophages and the like. In a preferred embodiment, the agonist peptide-pulsed antigen presenting cell is a dendritic cell.

The invention also provides a method of generating CEA and agonist peptide specific cytotoxic T lymphocytes in vivo or in vitro by stimulation of lymphocytes from a source with an effective amount of a agonist alone or in combination with a immunostimulatory molecule and/or adjuvant or in a liposome formulation. The sources of lymphocytes include but are not limited to peripheral blood, tumor tissues, lymph nodes and effusions such as pleural fluid or ascites fluid and the like.

The CEA and agonist peptide specific cytotoxic T lymphocytes of the present invention are immunoreactive with CEA agonist or peptide. The cytotoxic T lymphocytes inhibit the occurrence of tumor cells and cancer and inhibit the growth or kill expressing tumor cells expressing CEA or eptiopes thereof or agonist expressing tumor cells. The cytotoxic T lymphocytes, in addition to being antigen specific, are MHC class I restricted. In one embodiment the cytotoxic T lymphocytes are MHC class I HLA-A2 restricted. The cytotoxic T lymphocytes have a $CD8^+$ phenotype.

Selected patients bearing carcinoma cells expressing CEA or CEA epitopes are vaccinated subcutaneously up to three times at monthly intervals with DETOX™ adjuvant admixed with the appropriate peptide agonist may also be vaccinated carcinoma patients with autologous peripheral blood mononuclear cells pre-pulsed ex vivo with a peptide agonist alone or in combination with a peptide agonist. Anti-CEA T cell responses are evaluated as measured by proliferation assays.

Vaccination with CEA agonist peptides of the present invention induces highly specific and systemic anti-CEA cellular immune responses. Moreover, the development of such MHC class I-restricted agonist peptides has important implications for both active (i.e., vaccination) and passive (i.e., ex vivo expansion for cellular adoptive transfer) immunotherapies, which may be used for the induction and propagation of specific $CD8^+$ CTL responses in cancer patients.

Patients with solid tumors expressing CEA or epitopes thereof, including but not limited to colon cancer, lung cancer, pancreas cancer, endometrial cancer, breast cancer, thyroid cancer, melanoma, oral cancer, laryngeal cancer, seminoma, hepatocellular cancer, bile duct cancer, acute myeloblastic leukemia, basal cell carcinoma, squamous cell carcinoma, prostate cancer and the like benefit from immunization with the agonist peptides. Patients amenable to treatment using the agonist peptides of the present invention are those patients having tumors with CEA or CEA epitopes.

Peptides may be chemically synthesized under GMP conditions and purified by HPLC to >95% purity and lyophilized. Pharmaceutical compositions are formulated by reconstituting the peptide with a pharmaceutically acceptable carrier such as sodium chloride. In one example, each milliliter of solution contains 1500 μg of a agonist peptide plus 9.0 mg sodium chloride.

When the agonist peptide is administered with an adjuvant it is desirable to mix the peptide with the adjuvant shortly before administration to a patient.

The agonist peptide may be administered to a patient by various routes including but not limited to subcutaneous, intramuscular, intradermal, intraperitoneal, intravenous and the like. In one embodiment the agonist peptide is administered subcutaneously. The peptide may be administered at one or more sites to a patient. In one embodiment, the peptide, alone or in combination with an adjuvant, is administered into three sites subcutaneously, over the deltoids, the thighs and the abdomen.

In another method of generating an immune response, agonist peptide-pulsed antigen presenting cells are administered to the patient in an amount effective to generate an antigen specific immune response. The antigen presenting cells include but are not limited to dendritic cells, B lymphocytes, monocytes, macrophages and the like. In one embodiment, dendritic cells are isolated from a patient by methods described in Romani, N. et al (1994). The isolated dendritic cells are cultured in vitro with an agonist peptide for a period of about 0.5 to about 3 hours and washed to remove non-bound peptide. The agonist peptide-pulsed dendritic cells are transferred back into the patient at a concentration of about $10^6$ to about $10^9$ dendritic cells. Such a concentration is effective in generating an immune response in the patient including the generation of agonist peptide specific cytotoxic T lymphocytes which are able to inhibit the growth or kill tumor cells.

The criteria for determining an anti-tumor response in the immunized patient is as follows:
1. Complete Remission (CR): Complete disappearance of all evidence of tumor and return of abnormal tests to normal levels for a minimum of 4 weeks.
2. Partial Response (PR): Decrease by at least 50% in the sum of the products of the perpendicular diameters of all measured lesions in the absence of progression of any lesion nor the appearance of any new lesions for at least 4 weeks.
3. Stable Disease (SD): Change in measurable disease too small to meet the requirements for partial response or progression and the appearance of no new lesions for a period of at least 12 weeks. There may be no worsening of symptoms.
4. Progressive Disease (PD) or Relapse: Any one of the criteria below must be met to be considered progressive disease:
   Development of any new area of malignant disease (measurable or palpable),
   Increase (>25%) in any pretreatment area of measurable malignant disease.

The immunological response to immunization with the agonist peptides are assessed by in-vitro T cell proliferation assay and/or by in-vitro T cell cytotoxic assay before and after vaccination.

The present invention includes in vitro immunization for T cell proliferation and generation of cytotoxic T cell lines to the tumor specific agonist peptide. In vitro cultivation of peptide specific T cells from peripheral blood mononuclear cells (PBMC), lymph node tissue (LNT), or tumor infiltrating lymphocytes (TIL) with agonist peptide and IL-2 generates CEA and agonist peptide specific T cells. These T cells are tested for cytotoxicity against agonist peptide primed APC (autologous EBV transformed B cells or autologous tumor cells) has described herein. Generated T cell clones are characterized phenotypically by flow cytometry for express of CD3, CD4, and CD8. Agonist peptide specific cytotoxic lymphocytes may be adoptively transferred to a patient in order to inhibit or kill CEA or CEA epitopes expressing tumor cells. Patients may then be reimmunized with agonist peptide preferably in adjuvant.

Generally, between about $1\times10^5$ and $2\times10^{11}$ cytotoxic T cells per infusion are administered in, for example, one to three infusions of about 200 to about 250 ml each over a period of 30 to 60 minutes. After completion of the infusions, the patient may be treated with a biological response modifier such as interleukin 2 (IL-2). In the case of IL-2, recombinant IL-2 is administered intravenously in a dose of 720,000 IU per kilogram of body weight every eight hours. After adoptive transfer of the antigen specific cytotoxic T cells into the patient, the patient may be additionally treated with the agonist peptide used to prime the cytotoxic T cells, to further expand the T cell number in vivo.

The invention encompasses a DNA sequence and variants thereof which encode an agonist peptide.

In one embodiment the DNA sequence encoding the agonist peptide is a variant of the DNA sequence comprising:

```
TAC CTT TCG GGA GCG AAC
Tyr Leu Ser Gly Ala Asn

CTC AAC CTC              (SEQ. ID No: 6)
Leu Asn Leu.             (SEQ. ID No: 1)
```

One variant of SEQ. ID No: 6 includes but is not limited to a codon ATC (Ile) in place of the codon, CTC (Leu at position 7). Another variant of SEQ. ID No: 6 includes but is not limited to a codon, TGT (Cys) in place of the codon, AAC (Asn at position 6).

In another embodiment, the DNA sequence encoding the agonist peptide comprises:

```
TAC CTT TCG GGA GCG GAC
Tyr Leu Ser Gly Ala Asp

CTC AAC CTC              (SEQ. ID No: 7)
Leu Asn Leu              (SEQ. ID No: 2)
``` and variants thereof.

In yet another embodiment, the DNA sequence encoding the agonist peptide comprises:

```
TAC CTT TCG GGA GCG GAC
Tyr Leu Ser Gly Ala Asp

ATC AAC CTC              (SEQ. ID No: 8)
Ile Asn Leu              (SEQ. ID No: 3)
``` or variants thereof.

Included in the ambit of the invention are conservative substitutions based on codon degeneracy provided the modification results in a functionally equivalent agonist peptide or a peptide with enhanced immunogenicity.

The invention further provides vectors and plasmids comprising a DNA sequence encoding an agonist peptide. The vectors include but are not limited to *E. coli* plasmid, a *Listeria* vector and recombinant viral vector. Recombinant viral vectors including but not limited to orthopox virus, avipox virus, capripox virus, suipox virus, vaccinia, baculovirus, human adenovirus, SV40, bovine papilloma virus, and the like comprising the DNA sequence encoding an agonist peptide.

Recombinant agonist peptide can be obtained using a baculovirus expression system in accordance with the method of Bei et al *J. Clin. Lab. Anal.* 9:261-268 (1995). Recombinant viral vectors can be constructed by methods known in the art such as U.S. Pat. No. 5,093,258; WO96/10419 Cepko et al *Cell* 37:1053-1062 (1984); Morin et al *Proc. Natl. Acad. Sci USA* 84:4626-4630 (1987); Lowe et al *Proc. Natl. Acad. Sci USA* 84:3896-3900 (1987); Panicali & Paoletti, *Proc. Natl. Acad. Sci USA* 79:4927-4931 (1982); Mackett et al, *Proc. Natl. Acad. Sci USA* 79:7415-7419 (1982); WO 91/19803; Perkus et al *Science* 229:981-984 (1985); Kaufman et al *Int. J. Cancer* 48:900-907 (1991); Moss *Science* 252:1662 (1991); Smith and Moss *BioTechniques* November/December, p. 306-312 (1984); U.S. Pat. No. 4,738,846; Sutter and Moss *Proc. Natl. Acad. Sci USA* 89:10847-10851 (1992); Sutter et al *Virology* (1994); and Baxby and Paoletti *Vaccine* 10:8-9 (1992).

Host cells which may express the DNA encoding the agonist peptide carried by vectors or plasmids are prokaryotic and eukoryotic host cells and include but are not limited to *E. coli, Listeria, Bacillus* species, COS cells, Vero cells, chick embryo, fibroblasts, tumor cells, antigen presenting cells and the like. When the host cell is an antigen presenting cell, the host cell is an antigen presenting cell, the host cell should additionally express an MHC class I molecule.

We recently reported (11) evidence of CTL responses to CEA in patients immunized with rV-CEA. The 9-mer peptide CAP1 was employed to expand CTL in vitro because of: (a) its strong binding to HLA-A2, and (b) its non-identity to other members of the CEA gene family expressed on normal tissues. CTLs were generated from post-immunization PBMC of patients while preimmunization blood of the same patients failed to proliferate. In addition, CAP1 pulsed dendritic cells stimulated in vitro growth of -A2 restricted CTL from peripheral blood of unimmunized cancer patients (12). Finally when CTL were generated in vitro by stimulation with dendritic cells encoding full-length CEA mRNA, cytotoxicity against CAP1 was higher than activity against six other -A2 binding CEA peptides (S. Nair and E. Gilboa, personal communication or unpublished observation). Such results encourage the notion that CAP1 is an immunodominant epitope of the CEA molecule.

The present invention is intended to improve the immunogenicity of the CAP1 peptide by introducing amino acid substitutions at non-anchor positions to form the agonist peptides of the present invention. When using. T-Vac8 CTL as an effector, the analog CAP1-6D sensitized target cells for lysis far better than CAP1 itself. Further studies showed that cytolytic activity of a second -A2 restricted, CAP1 specific CTL, T-Vac24, was as good or greater with CAP1-6D than with CAP1. These demonstrations of enhanced reactivity could not be explained by improved presentation by class I MHC. Finally, CAP1-6D could be used to stimulate CTL in vitro from PBMC of both carcinoma patients and normal donors. Prior to the present invention, attempts to stimulate anti-CAP1 CTL from normal donors using this same methodology have been unsuccessful. The present invention relates to stimulation of normal donors with CAP1-6D as opposed to native CAP1 where stimulation with the native sequence failed to produce specific cytotoxic activity. In contrast, stimulation with CAP1-6D produced several CTL with specific anti-CAP1 peptide reactivity as well as anti-tumor reactivity. Thus, the analog peptide CAP1-6D is capable of selecting a population of CAP1 specific human CTL more efficiently than native CAP1. Such an agonist might find applications in the design of T cell directed vaccines against CEA-expressing carcinoma.

The present invention also relates to the more efficient generation and expansion of tumor specific T cells for adoptive immunotherapy. In recent years, much progress has been achieved in characterizing the tumor associated antigen peptides that can be presented to CTL by class I HLA antigens. In instances where mutations generate neo-antigens such as point mutated ras (35, 36), p53 (37, 38) or β-catenin (39) vaccination strategies target the novel sequence under the assumption that the immune system is not "tolerant" to an antigen it has never seen. More recently it has been proposed that neo-antigens may also arise through post-translational deamidations (29, 40). However, in many instances the intended targets of tumor therapy are not neoantigens but rather normal oncofetal or differentiation antigens that are overexpressed or ectopically expressed by malignant cells. Such is the case for. CEA (41). In such situations, models invoking "tolerance" predict that the immune system has encountered these antigens and is less able to respond to them. This classical picture has been challenged in recent years by numerous reports of immunity elicited to overexpressed differentiation antigens, oncogenes, and tumor suppressor genes (37, 38, 42-44). Nonetheless, it is often experimentally difficult to generate and expand T cells with desired anti-tumor activity and it is therefore desirable to devise new strategies for generating CTL.

Some class II binding-peptides have been described in which substitutions enhance responses of murine and human Th clones without increasing the binding to class II antigens (29, 45-47). Among human class I peptides, however, the only substitutions described for the generation of CTL were those that increase binding to HLA (17-20). The substitutions in those studies were directed to residues at the primary or secondary anchor positions that define the binding motifs to class I MHC antigens. Even substitutions directed to a non-anchor position (19) achieved their enhancing effect by increasing binding to HLA-A2. The analog CAP1-6D in the present report represents what appears to be a different class of substituted CTL peptides, agonists that enhance recognition of the peptide-MHC ligand by the T cell receptor and produce greater effector function without increases in binding. To our knowledge this is the first such enhancer agonist peptide described for a human CTL.

The increased lytic susceptibility of targets in the presence of CAP1-6D is unlikely to be due to better antigen presentation. Binding experiments show that HLA-A2 presents the native CAP1, and the analogs CAP1-6D and CAP1-71 approximately equally. Another possibility is that CAP1-6D shows increased activity because it is presented by more than one allele and T-Vac8 is promiscuous towards peptide-MHC complexes. However, T-Vac8, T-Vac24, and CTL derived from nonimmunized patients showed better lysis with CAP1-6D. Since HLA-A2 is the only class I MHC on the targets employed, the improved lysis cannot be accounted for by recruitment of another class I MHC.

Since anti-CAP1 CTL from multiple donors demonstrate agonist cross reactivity it is possible that CAP1-6D could be used to stimulate growth of CTL from numerous -A2 individuals. We are encouraged by the quite distinct differences between T-Vac8 and T-Vac24 in magnitude of response to the agonist; this implies that each effector utilizes different TCR gene segments and that nonetheless they can recognize both the native sequence and the CAP1-6D substitution. The ability of CAP1-6D to act as an agonist with T cells expressing different T cell receptors clearly magnifies its therapeutic potential. Thus, the present invention also relates to stimulation with the agonist and subsequent generation of T cells that recognize the normal sequence in non-immunized individuals. Such individuals have presumably never encountered the modified sequence and since the agonist is more efficient at triggering a T cell response, such agonists might be capable of selecting CTL more readily than immunogens based on the native sequence.

For peptide-derived CTL to be useful therapeutic reagents it is essential to demonstrate that they can lyse tumor cells that express endogenous antigen (48, 49). Previously (11), we had shown that tumor cells process CEA and present antigens recognized by CTL generated by stimulation with CAP1. In accordance with the present invention, CTL grown from the normal donors by stimulation with CAP1-6D are also capable of recognizing allogeneic CEA-positive, HLA-A2 positive tumor cells. These T cells fail to recognize -A2 negative tumor cells or -A2 positive cells that lack CEA expression.

We have also shown that CTL selected with the CAP1-6D agonist can be maintained subsequently by stimulation with the native CAP1 sequence. This is an important finding since CTL in patients, whether established in vivo through active immunization, or transferred adoptively after ex vivo expansion, will likely only encounter the native sequence. This allows the CTLs to be maintained over an extended duration in vivo.

One of the original reasons for selecting and testing CAP1 was its non-identity with other reported sequences in the human genome. It was therefore predicted that any immune responses attained would be unlikely to damage normal tissues bearing other antigens. For this reason a similar search of protein databases was undertaken for the peptides CAP1-6D and CAP1-7I and revealed that they are not reported as human sequences elsewhere in the Genebank (Genetics Computer Group, Madison, Wis.). However, two similar sequences, YLNVQDLNL (SEQ. ID No: 9) and YLHDPEFNL (SEQ. ID No: 10), are reported for antigens from African swine fever virus and measles virus, respectively. These sequences fit the consensus motif for HLA-A2 and therefore allow infected individuals to express cross-reacting antigens to CAP1. One interesting possibility is that the presence of anti-CAP1 CTL in some patients represents an example of epitope mimicry (50).

Two recent reports suggest that modified asparagine residues might enhance the immunogenicity of class I MHC peptides. Skipper et al. (40) used CTL generated in mixed lymphocyte tumor cell cultures to identify antigens in extracts of melanoma cells. One antigenic peptide was identical at 8 of 9 positions to a sequence from tyrosinase, with an asparagine to aspartic acid replacement at position 3. When tested using synthetic peptides, the CTL were more active against the aspartic acid peptide than against the peptide containing the genetically predicted asparagine. These authors speculate that post-translational deamidations can generate antigenic peptides from normal differentiation antigens. Recently, Chen et al. (51) reported generating murine CTL to a stabilized succinimide derivative of an asparagine-containing antigenic peptide. Although these CTL could kill targets pulsed with the natural asparagine peptide, they did so with less sensitivity. They raise the possibility that deamidation of proteins in vivo and in vitro can produce transient succinimide intermediates that represent altered self-ligands capable of eliciting an immune response. At the other extreme, Kersh and Allen (52) replaced a TCR contact asparagine with aspartic acid in a hemoglobin peptide and abolished responsiveness to a murine Th clone. Presently we cannot exclude the possibility that the enhanced reactivity of CAP1-6D is due to deamidation of the native sequence which in turn primes the response that we detect with CAP1. However, our repeated inability to raise anti-CAP1 CTL from pre-immunized PBMC of the same patients from whom we generated post-immunization CTL, argues against this. Also, putative deamidations could not account for the recognition of other analogs such as CAP1-6C or CAP1-7I by T-Vac8 CTL. Instead it seems more reasonable that T cell receptors from both T-Vac8 and T-Vac24, as well as the new lines described here, can recognize some deviation from the native CAP1 sequence.

In summary, synthesis of analogs of an immunodominant CEA peptide with amino acid substitutions at positions predicted to potentially interact with the T cell receptor allowed us to identify an enhancer agonist. This agonist was recognized by two different CEA CTL and increases the activity of one of them by 2-3 orders of magnitude. The agonist was also able to stimulate growth of CTL from peripheral blood of non-immunized normal donors with far greater facility than the native peptide sequence. Most important, the CTL generated using the enhancer agonist was able to recognize and lyse targets presenting the native sequence, including tumor cell lines expressing endogenous CEA. In accordance with the present invention, characterization of this enhancer agonist peptide facilitates more aggressive anti-tumor immunotherapies when employed as an immunogen in vivo, or for the ex vivo expansion of autologous anti-tumor CTL. The synthetic approach employed according to the present invention is also useful in improving immunogenicity of other peptide CTL epitopes.

MATERIALS AND METHODS

Peptides

A panel of single amino acid substitutions to positions p5 through p8 of the CEA peptide CAP1 were made by f-moc chemistry using pin technology (Chiron Mimotopes, Victoria, Australia). CAP1 (YLSGANLNL) and CAP1-6D (YLSGADLNL), greater than 96% pure, were also made by Multiple Peptide Systems (San Diego, Calif.). Additional peptides CAP1-7I and NCA571 were synthesized on an Applied Biosystems 432A synthesizer and were greater than 90% pure by C18 reverse-phase HPLC.

Cell Lines

T-Vac8 (53) and T-Vac24 (11) are human CTL specific for the CEA peptide CAP1. These cell lines were generated by in vitro stimulation of PBMC using CAP1 and IL-2, according to previously published methods (11). Briefly, post-immunization PBMC were from HLA-A2+ individuals with advanced carcinoma that had been administered rV-CEA in a Phase I trial. PBMC were isolated on gradients of lymphocyte separation medium (Organon Teknika, Durham, N.C.) and $2 \times 10^5$ cells were placed in wells of sterile 96 well culture plates (Coming Costar, Cambridge, Mass.) along with 50 µg/ml peptide. After 5 days incubation at 37° C. in a humidified atmosphere containing 5% $CO_2$, supernatants were removed and replaced with medium containing 10 U/ml human IL-2 (a gift of the Surgery Branch, NCI). Cultures were fed with IL-2 every 3 days for 11 days and then restimulated with irradiated (4000 rad) autologous PBMC ($5 \times 10^5$) and peptide. Fresh IL-2 was provided every third day and subsequent restimulations were done every 2 weeks. CTL are maintained in complete RPMI (GIBCO/BRL, Grand Island, N.Y.) medium with glutamine (GIBCO/BRL), penicillin, streptomycin and 10% pooled human AB serum (Gemini Bioproducts, Inc., Calabasas, Calif.).

Cell line C1R-A2 (provided by Dr. W. Biddison, National Institute of Neurological Disorders and Stroke, National Institutes of Health, Bethesda, Md.) is maintained in complete RPMI with 10% fetal bovine serum (FBS, Biofluids Inc., Rockville, Md.), glutamine, non essential amino acids and pyruvate (Biofluids) and 1 mg/ml G418. Cell line 174.CEM-T2 (provided by Dr. P. Creswell, Yale University School of Medicine, New Haven, Conn.) is defective in endogenous peptide processing and is maintained in Iscove's (GIBCO/BRL) with 10% FBS. Both C1R-A2 and T2 lines present exogenous peptides with HLA-A2.

CEA positive tumor cell lines SW480, SW1463, SW1116 and SW 837 were obtained from the American Type Culture Collection (ATCC, Rockville, Md.) and passaged weekly in respective culture medium described in the ATCC catalog. The CEA negative melanoma line SKmel24 (provided by Dr. S. Rosenberg, National Cancer Institute, National Institutes of Health, Bethesda, Md.) was passaged weekly in RPMI 1640, 10% FBS and 10 µg/ml gentamicin (Life Technologies). The CEA negative ovarian tumor CaOV3 was provided by Dr. R. Freedman (MD Anderson Cancer Center, Houston Tex.) and was cultured in RPMI with 15% FBS, glutamine, 12 µg/ml insulin (Sigma, St. Louis, Mo.), 10 µg/ml hydrocortisone (Biofluids) and 10 µg/ml gentamicin. All tumor lines were trypsinized with Trypsin/Versene (Biofluids) for 5-10 minutes prior to labeling with isotope for CTL assays. The highly sensitive natural killer (NK) target K562 was obtained from ATCC and passaged weekly with RPMI 1640, 10% FBS.

Generation of CTL

T cell lines T-N1 and T-N2 were generated from PBMC of two normal HLA-A2 positive donors by in vitro stimulation with peptide as follows. For the first stimulation cycle, T cells were positively selected by panning on CD3+ MicroCellector flasks (Applied Immune Sciences, Santa Clara, Calif.). CD3+ cells ($3 \times 10^6$) were cultured with $10^6$ 174.CEM-T2 cells that were previously infected with vaccinia virus expressing human B7 at a multiplicity of infection of 10, pulsed with 50 µg/ml CAP1 or CAP1-6D peptide and 2 µg/ml human β2 microglobulin (Intergen, Purchase, N.Y.), and irradiated (10,000 rad). Cultures were incubated at 37° C. in a humidified atmosphere containing 5% $CO_2$, in T25 flasks in RPMI with 10% human serum, 2 mM glutamine, and 10 µg/ml gentamicin in a total volume of 10 ml with $2 \times 10^7$ irradiated (2500 rads) autologous PBMC as feeder cells. After 24 hours in culture 10 U/ml huIL-2 and 0.1 ng/ml rIL-12 (R & D Systems, Minneapolis, Minn.) were added. After 9 days in culture, cells were restimulated using irradiated (10,000 rads) autologous EBV-B cells preincubated with 25 µg/ml peptide at a ratio of 2.5:1 stimulator cells to T cells, and IL-2 and IL-12 were again added 24 hours later. Peptide concentration was halved with each subsequent stimulation cycle until a final concentration of 3.12 µg/ml was achieved.

In addition, CTL were generated from post-immunization PBMC of cancer patient Vac8 by stimulation with CAP1-6D according to already published procedures (11).

CTL Assay

Target cells were labeled with $^{51}Cr$ or $^{111}In$, then incubated at 2,000-10,000 per well with or without peptides in round bottom microtiter plates (Corning Costar). One hour later, T cells were added. Supernatants were harvested (Skatron, Inc., Sterling Va.) after 4 hour and isotope release was measured. All assays were performed in triplicate and percent specific release was calculated according to:

$$\frac{(\text{observed release-spontaneous release})}{(\text{maximum release-spontaneous release})} \times 100$$

where spontaneous release is obtained by omitting the T cells, and maximum release is obtained by adding 1% Triton ×100.

Binding Assay

Binding of peptides to HLA-A2 was evaluated by incubation with processing defective 174.CEM-T2 cells and measuring the stability of cell surface peptide-A2 complexes (30). Briefly, cells were harvested and washed with serum-free RPMI then incubated overnight at $1-2 \times 10^6$ cells/well with various concentrations of peptides. The next day, cells were collected, washed in PBS with $Ca^{2+}$, $Mg^{2+}$ and 5% FBS, then divided into aliquots for single color flow cytometric analysis. Cells were incubated 1 hour on ice without antibody, with anti-A2 antibody A2, 69 (One Lambda, Inc., Canoga Park, Calif.) or with isotype-matched control antibody UPC-10 (Organon Teknika) then washed and stained 1 hour with fluorescein-isothiocyanate (FITC) goat anti-mouse Ig (Southern Biotechnology Associates, Birmingham, Ala.). Cell surface staining was measured in a Becton Dickinson flow cytometer (Mountain View, Calif.) and the mean fluorescence intensity (MFI) for 10,000 live cells was plotted against peptide concentration.

TCR Chain Usage

T-N1 CTL were cultured as described for 5 cycles of antigenic stimulation using the CAP1-6D analog. The line was then split and duplicate cultures were maintained either with CAP1 or CAP1-6D for 5 additional stimulation cycles. Ficoll-purified T cells ($5 \times 10^5$) were stained with a panel of 19 anti-Vβ and 2 anti-Vα murine monoclonal antibodies to human αβ T cell receptor variable regions. Cells were incubated with 10 µg/ml of purified antibodies for 30 minutes at 4° C. The unlabeled monoclonals used were: Vβ3.1 clone 8F10, Vβ5(a) clone 1C1, Vβ5(b) clone W112, Vβ5(c) clone LC4, Vβ6.7 clone OT145, Vβ8(a) clone 16G8, Vβ12 clone S511, Vβ13 clone BAM13, Vα2 clone F1 and Vα12.1 clone 6D6 (T Cell Diagnostics, Woburn, Mass.) and Vβ18 (Immunotech, Westbrook, Me.). Cells were stained with 10 µg/ml of FITC-labeled goat anti-mouse IgG antibody (Southern Biotechnology Associates) for 30 minutes in the dark. Directly labeled monoclonals were: FITC-labeled Vβ11, Vβ21.3, Vβ13.6, Vβ14, Vβ16, Vβ17, Vβ20 and Vβ22 and PE-labeled Vβ9 and Vβ23 (Immunotech). Cells were fixed with 1% paraformaldehyde, washed with FACSFlow buffer (Becton Dickinson) and analyzed using a Becton Dickinson flow cytometer.

EXAMPLES

CAP1 Substituted Peptides

Several factors were considered in deciding which positions to examine for effects on T cell activity. Sequencing and mapping experiments have defined a binding motif in which position 2 and the C-terminal (position 9 or 10) are critical for peptide presentation by HLA-A2 (for review, see 31). In addition, Tyr at position 1 has been identified as an effective secondary anchor (20, 32). Since the CEA peptide CAP1 already has the preferred amino acids at these three positions these residues were not altered. Instead, we focused attention on residues predicted to interact with the TCR in the hope of finding analogs that would stimulate human CAP1-specific cytotoxic T cells. X-ray crystallographic studies of several peptides bound to soluble HLA-A2 suggest that all binding peptides assume a common conformation in the peptide binding groove (33). When five model peptides were examined, residues 5 through 8 protrude away from the binding groove and are potentially available for binding to a TCR. Therefore a panel of 80 CAP1 analog peptides was produced in which the residues at positions 5 through 8 (p5-p8) were synthesized with each of the 20 natural amino acids. The peptides are designated CAP1-pAA, where p refers to the position in the peptide and AA refers to the replacement amino acid, using the single letter amino acid code; i.e., CAP1-6D in which position 6 is occupied by aspartic acid.

Enhanced CTL Sensitivity of Targets to CAP1-6D Analog

The effects of these amino acid substitutions on potential TCR recognition was studied using a CAP1 specific, HLA-A2 restricted human CTL line designated T-Vac8. Briefly, T-Vac8 was generated as described in Materials and Methods by in vitro peptide stimulation of PBMC from a patient that had been administered rV-CEA. For initial screening, T-Vac8 was used in a cytotoxicity assay to measure $^{111}In$ release from labeled C1R-A2 cells incubated with each member of the peptide panel (at three peptide concentrations). Spontaneous release from the targets (in the absence of T-Vac8) was determined for each individual peptide.

The results are presented in FIG. 1A through 1D. Of the 80 single amino acid substitutions, most failed to activate cytotoxicity of T-Vac8. However, six independent substitutions preserved reactivity. At position 5, three analogs CAP1-5F, CAP1-5I and CAP1-5S provided stimulation, albeit at reduced levels compared to CAP1 itself. At position 6 the substitutions CAP1-6C and CAP1-6D activated T-Vac8 cytotoxicity and seemed to be equal to or better than CAP1 since they were more active at the intermediate (0.1 µg/ml) peptide concentration. At position 7 analog CAP1-7I also appeared to be active. Finally, at position 8, no analogs were able to sensitize targets to lysis by T-Vac8. The two most active analogs (CAP1-6D and CAP1-7I) were then analyzed in detail, omitting CAP1-6C due to concern for disulfide formation under oxidizing conditions.

Figure 2A:
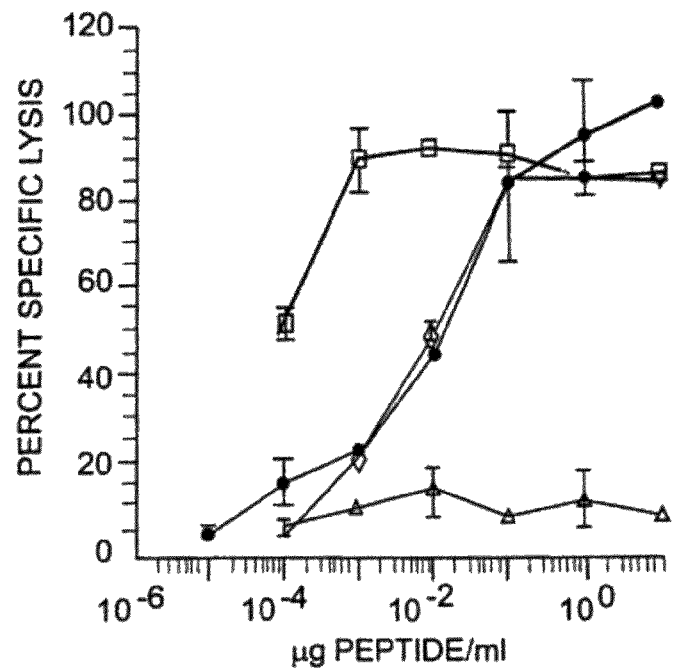
Figure 2B:
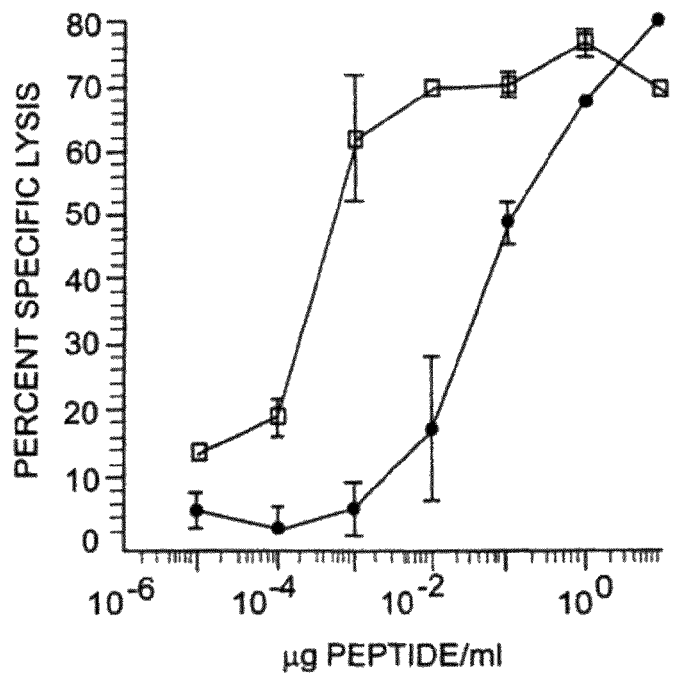

Purer preparations (90-96% pure) of native CAP1 and the analogs CAP1-6D and CAP1-7I were synthesized and compared in a CTL assay over a wider range of peptide concentrations, using two different cell lines as targets (FIGS. 2A and 2B). Employing T2 cells analog CAP1-6D was at least $10^2$ times more effective than native CAP1. CAP1-6D lytic activity was at ½ maximum at $10^{-4}$ μg/ml (FIG. 2A). In contrast, the CAP1-7I analog and the native CAP1 sequence were comparable with each other over the entire range of peptide titration and showed half maximal lysis at $10^{-2}$ μg/ml. Employing the C1R-A2 cells as targets, CAP1-6D was similarly between $10^2$ and $10^3$ more effective in mediating lysis than CAP1 (FIG. 2B).

The CAP1-6D peptide was also tested using a second CEA-specIfic T cell line, T-Vac24 (11). This line was generated from rV-CEA post vaccination PBMC of a different carcinoma patient by in vitro stimulation with the native CAP1 peptide; in contrast to predominantly CD8+ T-Vac8, T-Vac24 has a high percentage of CD4+CD8+ double positive cells (11). In a 4 hr $^{111}$In release assay employing T-Vac24, CAP1-6D was slightly more effective (30% lysis) than the native CAP1 sequence (20% lysis); although the differences were not as pronounced as with T-Vac8, the increased sensitivity to the analog was seen in three separate experiments. The analog peptide clearly engaged the lytic apparatus of a second CAP1 specific CTL.

Analogs and Native Peptide Show Identical Presentation by HLA-A2

The increased effectiveness of CAP1-6D in CTL assays could be due to better presentation by the target. The most active CAP1 analogs were tested for binding to HLA-A2 by measuring cell surface HLA-A2 in the transport-defective human cell line T2. When compared over a 4-log range of concentrations, native CAP1 and the two analogs CAP1-6D and CAP1-7I all presented equally on T2 cells (FIG. 3). In addition, dissociation experiments indicate that the HLA-A2 complexes that form with the 3 peptides show no appreciable differences in stability (FIG. 3—insert). When peptide-pulsed T2 cells were washed free of unbound peptide, the half lives of cell surface peptide-A2 complexes were 12.5 hrs (CAP1), 9.7 hrs (CAP1-6D), and 10.8 hrs (CAP1-7I). If anything, the complex formed with the agonist peptide seems slightly less stable. Since there are no differences in binding to HLA-A2, the improved effectiveness of CAP1-6D in the CTL assays appears to be due to better engagement by the T cell receptor, a behavior characteristic of an enhancer agonist peptide.

Human CTL Generated with CAP1-6D Also Recognize Native CAP1

The CAP1-6D agonist might be useful in both experimental and clinical applications if it can stimulate growth of CEA-specific CTL from patients with established carcinomas. In one experiment, post rV-CEA immunization PBMC from cancer patient Vac8 (the same rV-CEA patient from whom T-Vac8 CTL were established) were stimulated in vitro with CAP1-6D and after 5 rounds of stimulation were assayed for CTL activity against targets coated with CAP1 or CAP1-6D. This new line demonstrated peptide-dependent cytotoxic activity against target cells coated with either CAP1-6D or native CAP1 (Table 1).

Post immunization PBMC from patients Vac8 and Vac24 were already shown to produce CTL activity when stimulated with CAP1 while preimmunization PBMC were negative (11, 34). Moreover, previous attempts to stimulate CTL activity from healthy, non-immunized donors with the CAP1 peptide were unsuccessful. To test if the agonist peptide is indeed more immunogenic than native CAP1 we attempted to generate CTL from healthy, non-immunized donors using CAP1-6D. HLA-A2+ PBMC from apparently healthy individuals were stimulated in vitro either with CAP1 or the CAP1-6D agonist. After 4 cycles of in vitro stimulation, cell lines were assayed for specificity against C1R-A2 cells pulsed with either CAP1 or CAP1-6D.

While stimulations with CAP1 or the CAP1-6D peptide produced T cell lines, peptide specific lysis was only obtained in the lines generated with CAP1-6D. Two independent T cell lines from different donors were derived using CAP1-6D and were designated T-N1 and T-N2 (FIG. 4A and FIG. 4B respectively). Both CTL lines lyse C1R-A2 targets pulsed with native CAP1 peptide. However, more efficient lysis is obtained using the CAP1-6D agonist. T-N1 CTL recognizes CAP1-6D at a 3-10 fold lower peptide concentration than CAP1 and T-N2 recognizes the agonist 100 fold better than CAP1. In contrast, attempts to generate a CTL cell line from normal donors by stimulation with CAP1 resulted in lines with no peptide-dependent lysis and loss of the lines in early stimulation cycles. Thus the attempts to generate T cell lines using the two peptides demonstrated the ability of CAP1-6D to act as an agonist not only at the effector stage, in the lysis of targets, but also in selecting T cells that are presumably in low precursor frequencies.

To determine whether CTL established with the agonist could be maintained on the native CAP1 sequence, T-N1 was cultured for 5 cycles as described using CAP1-6D, then divided into duplicate cultures maintained on the agonist or on CAP1. T-N1 continued to grow when stimulated with either peptide and responded to both peptides in CTL assays. Phenotypic analysis of the TCR usage in T-N1 indicates that the majority of cells (71%) utilize Vβ12, with a minor population that utilize Vβ5.3 (Table 2). The same pattern of TCR Vβ usage was observed after switching the cells to CAP1 for 5 more stimulation cycles. This Vβ usage pattern was distinct from that of T-Vac8. These data indicate that the agonist can select T cells that are probably in low precursor frequency but that once selected, such CTL could be maintained with the native CAP1.

CTL Generated with CAP1-6D Specifically Lysed CEA$^+$, HLA-A2$^+$ Tumor Cells

Studies were conducted to determine the ability of CTL generated with the enhancer agonist to lyse human tumor cells endogenously expressing CEA. T-N1 and T-N2 were tested against a panel of tumor cells that are CEA$^+$/A2$^+$ (SW480 and SW1463), CEA+/A2$^-$ (SW1116) or CEA$^-$/A2$^+$ (CaOV3 and SKmel24). A T cell line (T-N2) from the normal donor was tested for the ability to lyse tumor targets endogenously expressing CEA. T-N2 CTL generated with the agonist lysed tumor cells expressing both CEA and HLA-A2 while exhibiting no titratable lysis of CEA$^-$/A2$^+$ SKmel24 melanoma cells (FIG. 5A). No significant lysis of K562 was observed. In contrast, cell lines generated by stimulation with native CAP1 showed no detectable antitumor activity (FIG. 5B). The HLA-A2.1 restriction of the T-N2 response to CEA positive tumor targets was further demonstrated by the specific lysis of a CEA positive HLA-A2.1 negative tumor cell, SW837 after infection with a vaccinia-A2.1 construct (rV-A2.1). No lysis was observed when SW837 targets were infected with the control wild type vaccinia without the A2.1 transgene (FIG. 6).

The ability of a CTL line (T-N1) derived from a second donor to kill carcinoma targets expressing endogenous CEA is shown in FIGS. 7A and 7B. T-N1 specifically lysed SW480 tumor cells. This is dramatically enhanced to 79% lysis by pretreatment of the tumor cells with IFN-γ, a treatment that increases the cell surface density of both HLA-A2 and CEA. The specificity of T-N1 killing is demonstrated by its inability to lyse CEA⁻/A2⁺ tumors such as the ovarian derived tumor CaOV3, the melanoma tumor SKmel24, or the NK target K562. Finally, restriction by HLA-A2 is demonstrated by the failure of T-N1 to lyse CEA⁺/A2⁻ SW1116 tumor cells. (FIG. 7A), even after IFN-γ treatment (FIG. 7B).

TABLE 1

CTL generated by stimulation with the CAP1-6D analog from PBMC of an HLA-A2 patient immunized with rVCEA

| Effector/target ratio | % Lysis | | |
|---|---|---|---|
| | no peptide | CAP1 | CAP1-6D |
| 25:1 | 10% | 41% | 40% |
| 6.25:1 | 0.5% | 38% | 46% |

T cells were assayed after 5 in vitro stimulations. Cytotoxic activity was determined in 4 hour release assay with peptide at 25 μg/ml.

TABLE 2

TCR usage of CTL line established on CAP1-6D agonist

| TCR usage[a] | T-N1[b] | | T-N1[c] | |
|---|---|---|---|---|
| | % positive | MFI | % positive | MFI |
| Vβ12 | 71 | 83 | 70 | 83 |
| Vβ5.3 | 18 | 47 | 20 | 57 |
| Vβ3.1 | 6 | 48 | 8 | 46 |
| Vβ8 | 3 | 30 | 6 | 26 |
| Vβ13.6 | 2 | 19 | 3 | 39 |
| Vβ12.1 | 3 | 43 | 3 | 40 |

[a]Determined by FACS analysis using a panel of 19 Vβ and 2 Vα antibodies (see Materials and Methods). Only positively staining antibodies are shown.
[b]CTL line selected and maintained on agonist CAP1-6D as described in the Materials and Methods section.
[c]CTL line selected on agonist CAP1-6D for 5 stimulation cycles, and maintained on CAP1 for an additional 10 cycles.

This invention has been described in detail including preferred embodiments thereof. However, it will be appreciated that those skilled in the art, upon consideration of this disclosure, may make modifications and improvements thereon without departing from the spirit and scope of the invention.

References referred to are incorporated herein by reference.

REFERENCES

1. Muraro, R., Wunderlich, D., Thor, A., Lundy, J., Noguchi, P., Cunningham, R., and Schlom, J. Definition by monoclonal antibodies of a repertoire of epitopes of carcinoembryonic antigen differentially expressed in human colon carcinoma versus normal adult tissues. Cancer Res., 45: 5769-5780 1985.

2. Steward, A. M., Nixon, D., Zamcheck, N., and Aisenberg, A. Carcinoembryonic antigen in breast cancer patients: serum levels and disease progress. Cancer, 33: 1246-1252, 1974.

3. Vincent, R. G. and Chu, T. M. Carcinoembryonic antigen in patients with carcinoma of the lung. J. Thor. Cardiovas. Surg., 66: 320-328, 1978.

4. Gold, J. M., Freedman, S. O., and Gold, Human anti CEA antibodies detected by radioimmunoelectrophoresis. Nature New Biology, 239: 60-62. 1973.

5. Pompecki, R. Presence of immunoglobulin G in human sera binding to carcinoembryonic antigen (CEA) and nonspecific crossreacting antigen (NCA). Eur. J Cancer, 16: 973-974, 1980.

6. Ura, Y., Ochi, Y., Hamazu, M., Ishida, M., Nakajima, K., and Watanabe, T. Studies on circulating antibodies against CEA and CEA like antigen in cancer patients. Cancer Lett., 25: 283-295, 1985.

7. Fuchs, C., Krapf, F., Kern, P., Hoferichter, S., Jager, W., and Kalden, J. R. CEA-containing immune complexes in sera of patients with colorectal and breast cancer-analysis of complexed immunoglobulin classes. Cancer Immunol. Immunother., 26:180-184, 1988.

8. LoGerfo, P., Herter, F. P., and Bennett, S. J. Absence of circulating antibodies to carcinoembryonic antigen in patients with gastrointestinal malignancies. Int. J. Cancer, 9: 344-348. 1972.

9. MacSween, J. M. The antigenicity of carcinoembryonic antigen in man. Int. J. Cancer, 15: 246-252. 1975.

10. Chester, K. A. and Begent, H. J. Circulating immune complexes (CIC), carcinoembryonic antigen (CEA) and CIC containing CEA as markers for colorectal cancer. Clin. Exp. Immunol., 58: 685-693, 1984.

11. Tsang, K Y., Zaremba, S., Nieroda, C. A., Zhu, M. Z, Hamilton, J. M., and Schlom, J. Generation of human cytotoxic T cells specific for human carcinoembryonic antigen epitopes from patients immunized with recombinant vaccinia-CEA vaccine. J. Natl. Cancer Inst., 87: 982-990. 1995.

12. Gadea, J., Brunette, E., Philip, M., Lyeriy, H. K., Philip, R., and Alters, S. Generation of antigen specific CTL using peptide and gene modified dendritic cells. Proc. Am. Assoc. Cancer Res. [abstr], 3154. 1996.

13. Marshall, J. L., Hawkins, M. J., Richmond, E., Tsang, K., and Schlom, J. A study of recombinant ALVAC-CEA in patients with advanced CEA-bearing cancers. J. Immunol. [abstr]. 19: 461. 1996.

14. Foon, K. A., Chakraborty, M., John, W. J., Sherraft, A., Kohler, H., and Bhattacharya-Chatterjee, M. Immune response to the carcinoembryonic antigen in patients treated with an anti-idiotype antibody vaccine. J. Clin. Invest., 96: 334-342, 1995.

15. Fagerberg, J., Samanci, A., Yi, Q., Strigard, K., Ryden, U., Wahren, B., and Mellstedt, H. Recombinant carcinoembryonic antigen and granulocyte-macrophage colony-stimulating factor for active immunization of colorectal carcinoma patients. J. Immunol. [abstr]. 19: 461. 1996.

16. Conry, R. M., Saleh, M. N., Schlom, J., and LoBuglio, A. F. Human immune response to carcinoembryonic antigen tumor vaccines. J. Immunother. [abstr], 18: 137, 1995.

17. Parkhurst, M. R., Salgaller, M. L, Southwood, S., Robbins, P. F., Sette, A., Rosenberg, S A., and Kawakami, Y. Improved induction of melanoma-reactive CTL with peptides from the melanoma antigen gp100 modified at HLA-A*0201-binding residues. J. Immunol., 157: 2539-2548, 1996.

18. Salgaller, M. L, Marincola, F. M., Cormier, J. N., and Rosenberg, S. A. Immunization against epitopes in the human melanoma antigen gp100 following patient immunization with synthetic peptides. Cancer Res., 56: 4749-4757, 1996.

19. Bakker, A. B. H., van der Burg, S. H., Huubens, R. J. F., Drijfhout, J. W., Melief, C. J., Adema, G. J., and Figdor, C. G. Analogues of CTL epitopes with improved MHC class-I binding capacity elicit anti-melanoma CTL recognizing the wild type epitope. Int. J. Cancer, 70: 302-309, 1997.

20. Pogue, R. R., Eron, J., Frelinger, J. A., and Matsui, M. Amino-terminal alteration of the HLA-A*0201-restricted human immunodeficiency virus pal peptide increases complex stability and in vitro immunogenicity. Proc. Nat. Acad. Sci., 92: 8166-8170, 1995.

21. Lipford, G., Bauer, S., Wagner, H., and Heeg, K. Peptide engineering allows cytotoxic T cell vaccination against human papilloma virus tumor antigen E6. Immunol., 84: 298-303. 1995.

22. Grey, H. M., Ruppert, J., Vitiello, A., Sidney, J., Kast, W. M., Kubo, R. T., and Sette, A. Class I MHC-peptide interactions: structural requirements and functional implications. Cancer Surv., 22: 37-49, 1995.

23. De Magistris, M. T. Alexander, J., Coggeshall, M., Altman, A., Gaeta, F. C A., Grey, H. M., and Sette, A. Antigen analog-major histocompatibility complexes act as antagonists of the T cell receptor. Cell, 68: 625-634. 1992.

24. Bertoletti, A., Sette, A., Chissari, F. V., Penna, A., Levrero, M., Carli, M. D., Fiaccadori, F., and Ferrari, F. Natural variants of cytotoxic epitopes are T cell receptor antagonists for antiviral cytotoxic T cells. Nature, 369: 407-410, 1994.

25. Klenerman, P., Rowland-Jones, S., McAdam, S., Edwards, J., Daenke, S., Lalloo, D., Koppe, B., Rosenberg, W., Boyd, D., Edwards, A., Giangrande, P., Phillips, R. E., and McMichael, A. J. Cytotoxic T cell activity antagonized by naturally occurring HIV-1 gag variants. Nature. 369: 403-407. 1994.

26. Kuchroo, V. K., Greer, J. M., Kaul, D., Ishioka, G., Franco, A., Sette, A., Sobel, R A., and Lees, M. B. A single TCR antagonist peptide inhibits experimental allergic encephalomyelitis mediated by a diverse T cell repertoire. J. Immunol., 153: 3326-3336. 1994.

27. Jameson, S. C. and Bevan, M. J. T cell receptor antagonists and partial agonists. Immunity, 2: 1-11, 1995.

28. Meier, U-C., Klenerman, P., Griffin, P., James, W., Koppe, B., Larder, B., McMichael, A., and Phillips, R. Cytotoxic T lymphocyte lysis inhibited by viable HIV mutants. Science. 270: 1360-1362. 1995.

29. Chen, Y., Matsushita, S., and Nishimura, Y. Response of a human T cell clone to a large panel of altered peptide ligands carrying single residue substitutions in an antigenic peptide: characterization and frequencies of TCR agonist and TCR antagonism with or without partial activation. J. Immunol., 157: 3783-3790. 1996.

30. Nijman, H. W., Houbiers, J. G., Vierboom, M. P., van der Hurg, S. H., Drijfhout, J. W., D'Amaro, J., Kenemans, P., Melief, C. J., and Kast, W. M. Identification of peptide sequences that potentially trigger HLA-A2.1-restricted cytotoxic T lymphocytes. Eur. J. Immunol., 23: 1215-1219, 1993.

31. Rammensee, H-G., Friede, T., and Stevanovic, S. MHC ligands and peptide motifs: first listing. Immunogenetics, 41: 178-228, 1995.

32. Ruppert, J., Sidney, J., Celis, E., Kubo, R. T., Grey, H. M., and Sette, A. Prominent role of secondary anchor residues in peptide binding to HLA-A2.1 molecules. Cell, 74.: 929-937. 1993.

33. Madden, D. R., Garboczi, D. N., and Wiley, D. C. The antigenic identity of peptide-MHC complexes: a comparison of the conformations of five viral peptides presented by HLA-A2. Cell, 75: 693-708, 1993.

34. Hamilton, J. M., Chen, A. P., Nguyen, B., Grem, J., Abrams, S., Chung, Y., Kantor, J., Phares, J. C., Bastian, A., Brooks, C., Morrison, G., Allegra, C. J., and Schlom, J. Phase I study of recombinant vaccinia virus (rV) that expresses human carcinoembryonic antigen (CEA) in adult patients with adenocarcinomas. Proc. Am. Soc. Clin. Oncol. [abstr], 961. 1994.

35. Abrams, S. I., Horan Hand, P., Tsang, K. Y., and Schlom, J. Mutant ras epitopes as targets for cancer vaccines. Semin. Oncol., 23: 118-134, 1996.

36. Elas, A. V., Nijman, H. W., Van Minne, C. E., Mourer, J. S., Kast, W. M., Melief, C. J. M., and Schrier, P. I. Induction and characterization of cytotoxic T lymphocytes recognizing a mutated p21 RAS peptide presented by HLA-A2010. Int. J. Cancer, 61: 389-396, 1995.

37. Houbiers, J. G. A., Nijman, H. W., van der Burg, S. H., Drijfhout, J. W., Kenemans, P., van de Velde, C. J. H., Brande, A., Momburg, F., Kast, W. M., and Melief, C. J. M. In vitro induction of human cytotoxic T lymphocyte responses against peptides of mutant and wild type p53. Eur. J. Immunol., 23:2072-2077, 1993.

38. Ropke, M., Regner, M., and Claesson, M. H. T cell mediated cytotoxicity against p53-protein derived peptides in bulk and limiting dilution cultures of healthy donors. Scand. J. Immunol., 42: 98-103, 1995.

39. Robbins, P. F., El-Gamil, M., Li, Y. F., Kawakami, Y., Loftus, D., Appella, E., and Rosenberg, S. A mutated β-catenin gene encodes a melanoma-specific antigen recognized by tumor infiltrating lymphocytes. J. Exp. Med. 183: 1185-1192, 1996.

40. Skipper, J. C. A., Hendrickson, R. C., Guiden, P. H., Brichard, V., van Pel, A., Chen, Y., Shabanowitz, J., Wolfel, T., Slingluff, C. L., Jr., Boon, T., Hunt, D. F., and Engelhard, V. H. An HLA-A2-restricted tyrosinase antigen on melanoma cells results from post-translational modification and suggests a novel pathway for processing of membrane proteins. J. Exp. Med., 183: 527-534, 1996.

41. Thompson, J. A., Grunert, F., and Zimmerman, W. Carcinoembryonic antigen gene family: molecular biology and clinical perspectives. J. Clin, Lab. Anal., 5: 344-366, 1991.

42. Van der Bruggen, P., Traversari, C., Chomez, P., Lurquin, C., De Plaen, E., Van den Eynde, B., Knuth, A., and Boon, T. A gene encoding an antigen recognized by cytotoxic T lymphocytes on a human melanoma. Science, 254: 1643-1647, 1991.

43. Kawakami, Y., Eliyahu, S., Delgaldo, C. H., Robbins, P. F., Rivoltini, L., Topalian, S. L, Miki, T., and Rosenberg, S. A. Cloning of the gene coding for a shared human melanocyte antigen recognized by autologous T cells infiltrating into tumor. Proc. Natl. Acad. Sci., 91: 3515-3519. 1994.

44. Peoples, G. E., Goedegebuure, P. S., Smith, R., Linehan, D. C., Yoshino, I., and Eberlein, T. J. Breast and ovarian cancer-specific cytotoxic T lymphocytes recognize the same HER2/neu-derived peptide. Proc. Nat. Acad. Sci. 92: 432-436, 1995.

45. Matsuoka, T., Kohrogi, H., Ando, M., Nishimura, Y., and Matsushita, S. Altered TCR ligands affect antigen-presenting cell responses: up regulation of IL-12 by analogue peptide. J. Immunol., 157:4837-4843. 1996.

46. Ikagawa, S., Matsushita, S., Chen, Y-Z, Ishikawa, T., and Nishimura, Y. Single amino acid substitutions on a Japanese cedar pollen allergen (Cry j 1)-derived peptide induced alterations in human T cell responses and T cell receptor antagonism. J. Aller. Clin. Immunol., 97: 53-64, 1996.

47. England, R. D., Kullberg, M. C., Cornette, J. L., and Berzofsky, J. A. Molecular analysis of a heteroclitic T cell response to the immunodominant epitope of sperm whale myoglobin: Implications for peptide partial agonists. J. Immunol., 155: 4295-4306, 1995.

48. Ropke, M., Hald, J., Guldberg, P., Zeuthen, J., Norgaard, L, Fugger, L., Svejgaard, A., Van Der Burg, S., Nijman, H. W., Melief, C. J. M., and Claesson, M. H. Spontaneous human squamous cell carcinomas are killed by a human cytotoxic T lymphocyte clone recognizing a wild-type p53-derived peptide. Proc. Nat. Acad. Sci., 93: 14704-14707, 1996.

49. Correale, P., Walmsley, K., Nieroda, C., Zaremba, S., Zhu, M., Schlom, J., and Tsang, K. Y. In vitro generation of human cytotoxic T lymphocytes specific for peptides derived from prostate-specific antigen. J. Natl. Cancer Inst., 89: 293-300, 1997.

50. Wucherpfennig, K. W. and Strominger, J. L. Molecular mimicry in T cell-mediated autoimmunity: viral peptides activate human T cell clones specific for myelin basic protein. Cell, 80: 695-705, 1995.

51. Chen, W., Ede, N J., Jackson, D. C., McCluskey, J., and Purcell, A. W. CTL recognition of an altered peptide associated with asparagine bond rearrangement: Implications for immunity and vaccine design. J. Immunol., 157: 1000-1005, 1996.

52. Kersh, G. J. and Allen, P. M. Structural basis for T cell recognition of altered peptide ligands: A single T cell receptor can productively recognize a large continuum of related ligands. J. Exp. Med 184: 1259-1268, 1996.

53. Tsang, K. Y. Zhu, M. Z. Nieroda, C. A, Correale, P., Zaremba, S., Hamilton, J. M., Cole, D., Lam, C., and Schlom, J. Phenotypic Stability of a Cytotoxic T Cell Line Directed Against an Immunodominant Epitope of Human Carcinoembryonic Antigen (accepted by Clinical Cancer Res.).

We claim:

1. An isolated DNA sequence encoding an amino acid sequence comprising SEQ ID NO: 2, SEQ ID NO: 3, SEQ ID NO: 4, SEQ ID NO: 5, or combinations thereof.

2. The isolated DNA sequence of claim 1, wherein the amino acid sequence comprises SEQ ID NO: 2.

3. The isolated DNA sequence of claim 1, wherein the amino acid sequence comprises SEQ ID NO: 3.

4. The isolated DNA sequence of claim 1, wherein the amino acid sequence comprises SEQ ID NO: 4.

5. The isolated DNA sequence of claim 1, wherein the amino acid sequence comprises SEQ ID NO: 5.

6. A vector comprising a DNA sequence encoding an amino acid sequence comprising SEQ ID NO: 2, SEQ ID NO: 3, SEQ ID NO: 4, SEQ ID NO: 5, or combinations thereof.

7. The vector of claim 6, wherein the amino acid sequence comprises SEQ ID NO: 2.

8. The vector of claim 6, wherein the amino acid sequence comprises SEQ ID NO: 3.

9. The vector of claim 6, wherein the amino acid sequence comprises SEQ ID NO: 4.

10. The vector of claim 6, wherein the amino acid sequence comprises SEQ ID NO: 5.

11. An isolated cell comprising the vector of claim 6.

12. The isolated cell of claim 11, wherein the amino acid sequence comprises SEQ ID NO: 2.

13. The isolated cell of claim 11, wherein the amino acid sequence comprises SEQ ID NO: 3.

14. The isolated cell of claim 11, wherein the amino acid sequence comprises SEQ ID NO: 4.

15. The isolated cell of claim 11, wherein the amino acid sequence comprises SEQ ID NO: 5.

* * * * *